(12) United States Patent
Berry et al.

(10) Patent No.: US 10,994,082 B2
(45) Date of Patent: May 4, 2021

(54) INHALER COUNTER

(71) Applicant: ASTRAZENECA AB, Södertälje (SE)

(72) Inventors: Simon Christopher Berry, Mölndal (SE); Jonas Christiansen, Hasselager (DK); Svend Erik Elgaard, Struer (DK); Esben W. Johansen, Struer (DK); Claus Schmidt Moller, Fredensborg (DK); Jorgen Rasmussen, Struer (DK); Henrik Hougaard Vilstrup, Struer (DK); William Richard Treneman, Edmunds Suffolk (GB)

(73) Assignee: ASTRAZENECA AB, Sodertalje (SE)

( * ) Notice: Subject to any disclaimer, the term of this patent is extended or adjusted under 35 U.S.C. 154(b) by 442 days.

(21) Appl. No.: 16/129,190

(22) Filed: Sep. 12, 2018

(65) Prior Publication Data
US 2019/0175849 A1   Jun. 13, 2019

Related U.S. Application Data

(63) Continuation of application No. 14/344,153, filed as application No. PCT/GB2012/052240 on Sep. 12, 2012, now abandoned.

(30) Foreign Application Priority Data

Sep. 14, 2011  (GB) .................................... 1115874

(51) Int. Cl.
*A61M 15/00*  (2006.01)
(52) U.S. Cl.
CPC ...... *A61M 15/0075* (2014.02); *A61M 15/009* (2013.01); *A61M 15/0025* (2014.02);
(Continued)

(58) Field of Classification Search
CPC .......... A61M 15/0025; A61M 15/0026; A61M 15/007; A61M 15/0071; A61M 15/0075;
(Continued)

(56) References Cited

U.S. PATENT DOCUMENTS 2,541,161 A   2/1951  Harper et al.
4,817,822 A   4/1989  Rand et al.
(Continued)

FOREIGN PATENT DOCUMENTS

GB         294904       9/1928
JP     556-164114 U   12/1981
(Continued)

OTHER PUBLICATIONS

International Search Report issued in International Patent Application No. PCT/GB2012/052240, dated May 8, 2013.

*Primary Examiner* — Timothy A Stanis

(57) ABSTRACT

An inhaler for delivery of a medicament by inhalation is disclosed. The inhaler comprises a dispensing mechanism, the dispensing mechanism being configured to dispense a dose of medicament on actuation. The inhaler further comprises a dose counting mechanism comprising a counter and a translating member. The translating member comprises a pawl. The counter comprises a first count wheel, a second count wheel and an intermediate wheel engaged with the second count wheel and in selective engagement with the first count wheel. When the inhaler is fired to dispense a dose of medicament, the dispensing mechanism moves the translating member in a substantially linear direction. The pawl thus rotates the first count wheel, and as the first count wheel rotates, the intermediate wheel is selectively engaged thereby selectively rotating the second count wheel to count the doses of the inhaler.

19 Claims, 18 Drawing Sheets

(52) U.S. Cl.
CPC .... *A61M 15/0026* (2014.02); *A61M 15/0081* (2014.02); *A61M 15/0091* (2013.01); *A61M 15/008* (2014.02); *A61M 15/0096* (2014.02); *A61M 2205/27* (2013.01); *A61M 2205/276* (2013.01); *A61M 2205/585* (2013.01)

(58) Field of Classification Search
CPC ............ A61M 15/0081; A61M 15/009; A61M 15/0091; A61M 15/0096; A61M 2205/27
See application file for complete search history.

(56) References Cited

U.S. PATENT DOCUMENTS

| | | |
|---|---|---|
| 5,482,030 A | 1/1996 | Klein |
| 5,498,243 A | 3/1996 | Vallelunga et al. |
| 2004/0255935 A1 | 12/2004 | Bruna et al. |
| 2008/0156321 A1 | 7/2008 | Bowman et al. |
| 2010/0192946 A1 | 8/2010 | Oi et al. |

FOREIGN PATENT DOCUMENTS

| | | |
|---|---|---|
| JP | H9-247774 A | 9/1997 |
| WO | WO 1996/16687 A1 | 6/1996 |
| WO | WO 1998/52634 A1 | 11/1998 |
| WO | WO 2004/041334 A2 | 5/2004 |
| WO | WO 2006/026754 A2 | 3/2006 |
| WO | WO 2008/082359 A1 | 7/2008 |
| WO | WO 2008/110584 A2 | 9/2008 |
| WO | WO 2009/041662 A1 | 4/2009 |
| WO | WO 2009/103711 A1 | 8/2009 |
| WO | WO 2010/042036 A1 | 4/2010 |

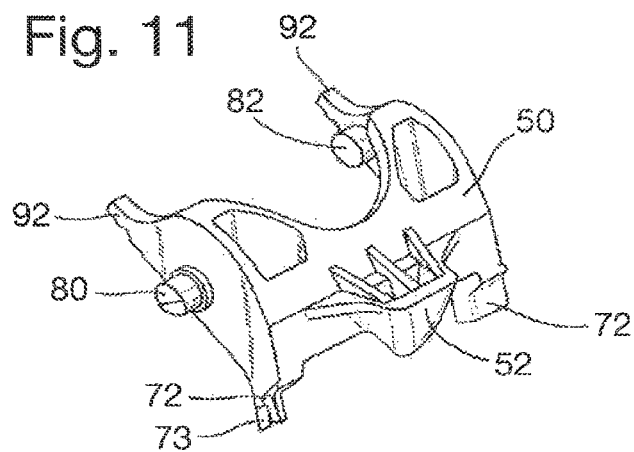
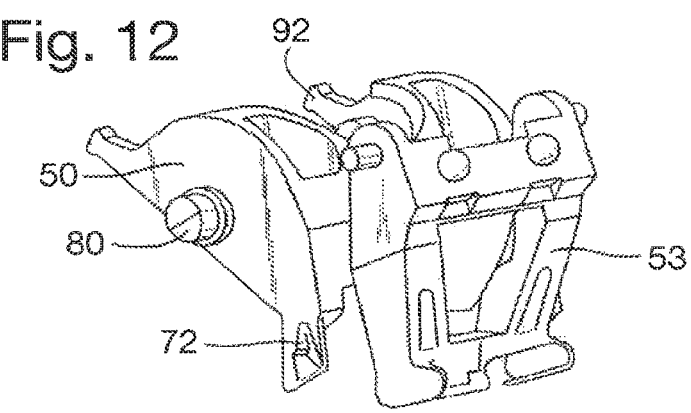
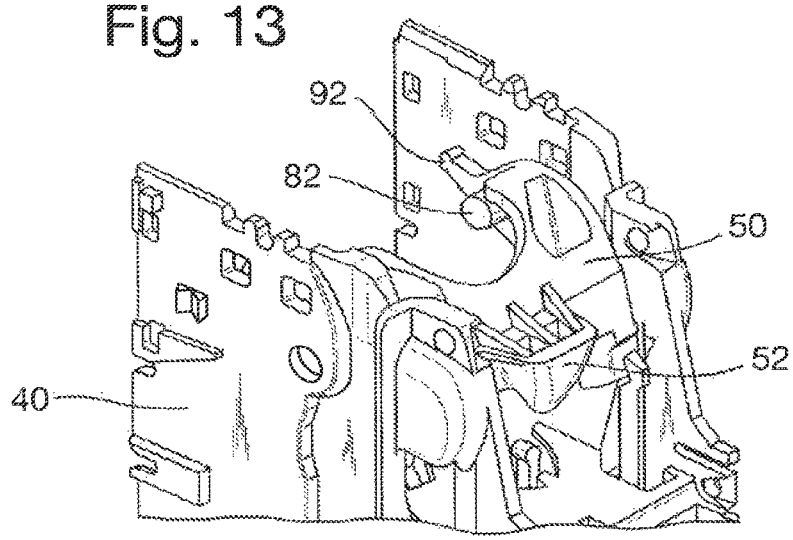

Figs. 21(a) -21(d)
Fig. 21(a)
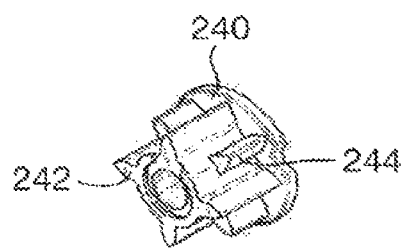
Fig. 21(b)
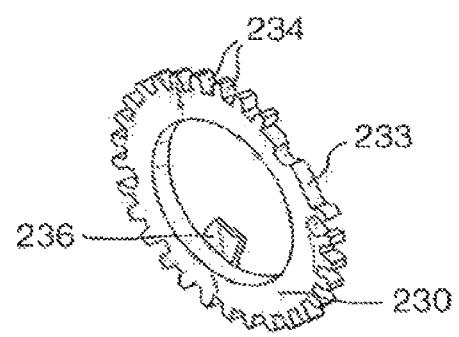
Fig. 21(c)
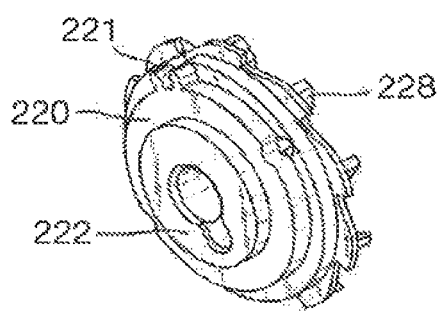
Fig. 21(d)
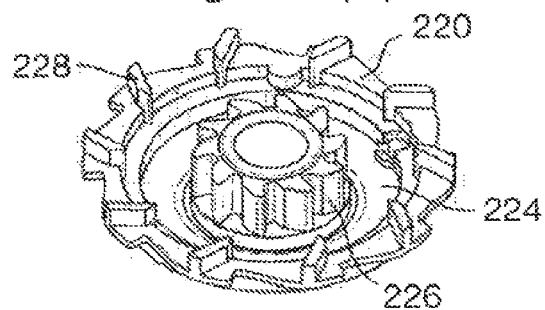

Figs. 22(a)-22(b)
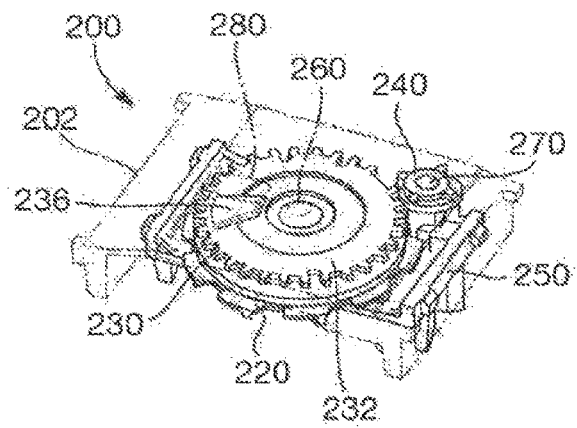
Fig. 22(a)
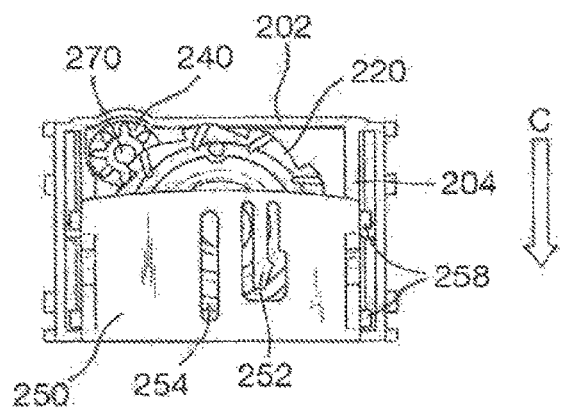
Fig. 22(b)

INHALER COUNTER

CROSS-REFERENCE TO RELATED APPLICATIONS

This application is a continuation of U.S. patent application Ser. No. 14/344,153, filed Sep. 12, 2012, said U.S. application Ser. No. 14/344,153 is a U.S. National Stage application of International Application No. PCT/GB2012/052240, filed on Sep. 12, 2012, which claims the benefit of priority to GB Application No. 1115874.8, filed Sep. 14, 2011. Each of the above listed applications is incorporated by reference herein in its entirety for all purposes.

TECHNICAL FIELD

The present invention relates to an inhaler for delivery of a medicament by inhalation and in particular to the mechanisms of the inhaler for dispensing of a dose of medicament and counting the dispensed dose.

BACKGROUND OF THE INVENTION

Inhalers are commonly used for delivery of a wide range of medicaments. In a dry powder inhaler (DPI) a dose of powdered substance is entrained in an air stream to deliver a dose of medicament through a mouthpiece to a user. In a pressurised metered dose inhaler (pMDI) a canister containing medicament in the inhaler is actuated, e.g. by compression, to deliver a metered dose of the medicament through a mouthpiece to a user. The inhaler may be configured to deliver a dose of medicament automatically. For example the inhaler may comprise an actuation mechanism to actuate the canister or to deliver the powdered substance when triggered. The actuation mechanism may be breath actuated, i.e. triggered by inhalation of a user through a mouthpiece. This ensures that a dose of medicament is dispensed whilst the user is inhaling, which is particularly advantageous since dispensing of a dose of medicament is co-ordinated with inhalation of the dose.

A breath-actuated pMDI inhaler is described in WO2008/082359. The inhaler actuation mechanism is operable to compress a canister of medicament to deliver a dose of medicament in response to inhalation by a user. The actuation mechanism comprises a loading mechanism to bias compression of the canister. A trigger mechanism holds the loading mechanism against compression of the canister. When a user inhales through a mouthpiece, the trigger mechanism releases the loading mechanism to compression of the canister to deliver a dose of medicament. A resetting mechanism interacts with a mouthpiece cover such that movement of the cover into a closed position resets the actuation mechanism.

The inhaler of WO2008/082359 Optionally has a registration module responsive to actuation of the inhaler, which can indicate, for example, the number of doses of medicament remaining in the canister. For patient safety, the inhaler must not dispense a dose of without counting the dispensed dose, as this may lead to the patient erroneously believing that there are remaining doses in an empty inhaler. The inhaler must also not decrement the count of the dose counter if a dose is not dispensed, since the patient may erroneously believe that no doses remain in the inhaler and a significant number of doses may be wasted when the inhaler is disposed of prematurely. Furthermore, the dose counter display must be sufficiently clear for a patient to be able to reliably and accurately read the display. For example, if the dose counter displays the number of doses remaining in the inhaler, if there is any ambiguity or lack of clarity with the displayed digits, the patient may believe that there are more doses remaining than is actually the case, which is dangerous for the patient, or may believe that there are fewer doses than actually remain, and may dispose of the inhaler too soon, wasting medicament.

SUMMARY OF THE INVENTION

In accordance with the present invention, there is provided an inhaler for delivery of a medicament by inhalation which overcomes the drawbacks of the prior art. This is achieved by the inhaler as defined in the independent claims.

From a first broad aspect, there is provided an inhaler for delivery of a medicament by inhalation, the inhaler comprising:

a dose counting mechanism comprising a counter and a translating member, the translating member comprising a pawl and the counter comprising a first count wheel, a second count wheel and an intermediate wheel engaged with the second count wheel and in selective engagement with the first count wheel, a dispensing mechanism configured, on actuation, to dispense a dose of medicament, wherein:

on actuation, the dispensing mechanism moves the translating member in a substantially linear direction, whereby the pawl rotates the first count wheel, and as the first count wheel rotates, the intermediate wheel is selectively engaged thereby selectively rotating the second count wheel.

Thus there is provided an improved inhaler for dispensing a plurality of metered doses of medicament to a patient, the inhaler having a counting mechanism for reliably and accurately counting each time a dose is dispensed and for displaying the dose count to the patient. This is achieved by moving a first count wheel in response movement of the dispensing mechanism, thus connecting the dispensing action simultaneously with the counting action and minimising or eliminating the possibility that one action could occur without the other. However the dispensing mechanism moves the translating member, for example by movement of a component of the dispensing mechanism, whether that movement is linear; rotational or a combination of both, this is translated into linear motion of a pawl of the translating member. In particularly preferred embodiments, the translating member is moved linearly by the dispensing mechanism. Preferably, the translating member and the counter are substantially in constant engagement and itis not necessary to disengage the components during counting or resetting.

The pawl engages the first count wheel and rotates the wheel reliably and consistently each time the pawl moves linearly in a first (counting direction). In turn, rotation of the first count wheel is selectively translated to the second count wheel by the intermediate wheel. For example, in a preferred embodiment, the first count wheel xci engages the intermediate wheel only once for each full rotation (i.e. through about 360°) of the first count wheel. The pawl of this embodiment only rotates the first count wheel in incremental portions of a full rotation (e.g. by about 36°) on each full movement in the counting direction, thus the first count wheel will rotate in incremental steps until a full rotation is achieved, at which time the first count wheel engages the intermediate count wheel, which in turn rotates the second count wheel, preferably by an amount considerably less than a full rotation.

Preferably the first count wheel is provided with members for receiving and engaging the pawl, such as teeth, preferably curved teeth, with notches therebetween. Such a ratchet arrangement ensures good engagement between the pawl and the first count wheel and thus consistent rotation of the wheel by movement of the pawl in the counting, direction.

Embodiments of the present invention are defined in the dependent claims.

In a particularly preferred embodiment, the first count wheel is incremented by $1/10^{th}$ of a full rotation upon each actuation by the pawl of the translating member (i.e. by about 36°). Preferably in this embodiment the first count wheel only engages with the intermediate wheel after one full rotation of the first count wheel, thus the first count wheel engages with the intermediate wheel after 10 actuations by the pawl, and rotates the second count wheel by an increment of its full rotation. Preferably the second count wheel is incremented by between no more than ½ a rotation (about 180°) and less than $1/40^{th}$ of a rotation (about 9°), more preferably by between no more than $1/10^{th}$ of a rotation (about 36°) and less than $1/20^{th}$ of a rotation (about 18°), more preferably by between no more than $1/12^{th}$ of a rotation (about 30°) and less than $1/15^{th}$ of a rotation (about 24°), more preferably by about $1/12^{th}$ of a rotation (about 30°).

Preferably in the above embodiments, the first count wheel comprises a set of first count numbers printed, embossed, or otherwise displayed annularly thereon, and preferably the second count wheel comprises a set of second count numbers printed, embossed or otherwise displayed annularly thereon. In a particularly preferred embodiment, the first count wheel comprises the numbers 0 to 9 arranged annularly and regularly spaced about a front face thereof and is incremented by $1/10^{th}$ of a full rotation (about 36°) upon each actuation by the pawl. Furthermore, in preferred embodiments, the second count wheel comprises the numbers 0 to 12 arranged annularly and regularly spaced about a front face thereof and is incremented by $1/12^{th}$ of a full rotation (about 30°) upon each actuation by the intermediate wheel. The intermediate wheel selectively engages upon each full rotation of the first count wheel (i.e. after 10 incremental actuations) and thus rotates the second count wheel by a single $1/12^{th}$ increment (i.e. about 30°) every time the first count wheel has counted 10 dispensed doses. In this way a dose counting mechanism that can decrement a counter from any of 129 to 120 doses through each individual dose count down to zero is provided. Of course, with embodiments for counting 150 doses, the second count wheel comprises the numbers 0 to 15 arranged annularly and regularly spaced about a front face thereof and is incremented by $1/15^{th}$ of a full rotation (about 24°) upon each actuation by the intermediate wheel, for embodiments for counting 200 doses, the second count wheel comprises the numbers 0 to 20 arranged annularly and regularly spaced about a front lace thereof and is incremented by $1/20^{th}$ of a full rotation (about 18°) upon each actuation by the intermediate wheel, or any other number of doses from 10 to 400 is envisaged within the scope of the invention. Although the number of doses that can be reliably displayed may be constrained by the size of the components of the counting mechanism or indeed by the size of the inhaler itself. Furthermore, the increments by which the wheels are fumed do het need to correspond with the numbers displayed on the front face of the count wheels and it is possible, for example, to increment the count wheels in steps smaller than the number of doses to be displayed, particularly if it is desired to have an end of life component, such as a zero dose indicator flag as part of one or both of the count wheels, as discussed below.

The front face (i.e. the displayed face) of the first count wheel and/or of the second count wheel preferably comprises not only numerical means to indicate the number of doses (remaining in or dispensed from the inhaler), but also other indicia. In a preferred embodiment, the counter comprises a low dose indicator, preferably a suitably coloured component so as to be readily visible when displayed, to indicate that the number of doses remaining in the inhaler is fewer than a predetermined number. This enables the patient to receive a warning that a new inhaler should be obtained so as to be ready to replace the present inhaler when empty. In a preferred embodiment, the low dose indicator comprises a portion of the front face of the second count wheel, which is preferably coloured, yellow or amber. Preferably the coloured portion is a background to the final numbers of the second count wheel, for example as a background to the numbers 2 and 1 (and zero if a 0 is displayed) to indicate when the remaining doses count is down to 20 or fewer doses.

Preferably the counter further or alternatively comprises a zero dose indicator, preferably a suitably coloured component so as to be readily visible when displayed, to indicate that there are no doses remaining in the inhaler. In preferred embodiments, the zero dose indicator comprises a red background to the numbers on the front face of one or both of the first and second count wheels. However in a particularly preferred embodiment, the zero dose indicator comprises a flag portion of the second count wheel, the flag protruding from the second-count wheel and overlapping the first count wheel. Preferably the flag is a distinctive colour, such as red and/or is distinctively marked or patterned, such that it is very clear when it is displayed on inhaler. Thus, when the intermediate wheel rotates the second count wheel after the last dose is dispensed, the flag moves into the display area and also covers the display of the first count wheel. This is advantageous because, even if the first count wheel continues to turn, no dose is visible to the patient and there is no confusion as to whether any doses remain. In a particularly preferred embodiment, the counting mechanism is configured such that, once the zero dose indicator has rotated into the display, it is not possible to rotate the second count wheel any further and thus the flag will remain in the display. This is preferably achieved by a suitable toothed arrangement, for example a missing tooth or set of teeth from the second count wheel to prevent further rotation of the flag, or the like. In such an arrangement, if it is desired to indicate 120 doses, the second count wheel should be incremented by less than $1/12^{th}$ of a full rotation (about 30°) upon actuation by the intermediate wheel, for example by $1/13^{th}$, $1/14^{th}$, $1/15^{th}$ (about 28°, 26° or 24° respectively) or even less of full rotation, thus providing a region of the front face of the second count wheel on which a flag or other zero dose indication member can be provided separately from the number of doses.

In accordance with embodiments of the present invention, the intermediate wheel is selectively engaged with the first count wheel and thus is selectively rotated by the first count wheel. This may be achieved by any suitable mechanism. For example at least one of the first count wheel and/or the intermediate wheel could be selectively moved, linearly or otherwise, into and out of engagement with the other wheel. Preferably however at least one of the first count wheel and/or the intermediate wheel is configured such that the wheels engage only at one or more predetermined positions during rotation of the first count wheel. In a particularly preferred embodiment, the first count wheel comprises a notch or other recess on an outer periphery thereof, for receiving a tooth or other protrusion of the intermediate wheel. Preferably the first count wheel comprises a single notch such that only once every full rotation is the intermediate wheel tooth engaged in the notch, as it passes the intermediate wheel. Of course, it is envisaged that the first count wheel may comprise a plurality of notches, evenly or otherwise spaced apart to engage the intermediate wheel more than once per fall rotation.

The intermediate wheel may be of any suitable configuration. Preferably the intermediate wheel comprises a plurality of evenly spaced teeth about an outer periphery thereof. As the notch (or a notch of a plurality of notches) of the first count wheel comes into alignment with one of the intermediate wheel teeth, the notch engages with the tooth and rotates the intermediate wheel by a predetermined increment which is preferably substantially less than a full rotation of the intermediate wheel. In preferred embodiments the intermediate wheel comprises a suitable number of teeth for engagement with the notch of the first count wheel, for example it is particularly preferred for the intermediate wheel to comprise four evenly spaced teeth. Of course the arrangement of the intermediate wheel and first count wheel could be the opposite of the above, i.e. the teeth may be present on the first count wheel and the notch forth part of the intermediate wheel or the like.

Preferably the intermediate wheel further comprises a second set of evenly spaced teeth, preferably four thereof, interspersed with the teeth for engagement with the first count wheel. The second set of evenly spaced teeth are configured for engagement with notches between teeth of the second count wheel, which is fully engaged with the intermediate wheel and is rotated thereby every time the intermediate wheel is rotated. In preferred embodiments, the second count wheel engages with each and every tooth of the intermediate wheel. Thus the first count wheel rotates the intermediate wheel only, when the wheels engage, which is preferably every $10^{th}$ increment of the first count wheel, but the intermediate wheel rotates the second count wheel on every incremental rotation of the intermediate wheel. In this manner a single digit count can be implemented by the first count wheel (which could therefore be referred to as a 'units' wheel) and a count every tenth increment of the first count wheel can be effected by the second count wheel (which could therefore be referred to as the 'tens' wheel).

The interactions and engagement between the wheels of the dose counting mechanism can be achieved in any suitable manner. Preferably the wheels are aligned relative to each other on suitably configured rotation axes. In a particularly preferred embodiment, the dose counting mechanism comprises a counter chassis, having a first and a second axis protruding therefrom, the first axis spaced from the second axis. The first axis is configured to receive the first and second count wheels co-axially thereon such that the digits annularly displayed on the front face of the first count wheel are displayed within and concentrically with the digits annularly displayed on the front face of the second count wheel. Namely the units are displayed inside the tens thus providing a display showing numbers that can be incremented or decremented as single digits upwards from zero to hundreds or downwards from hundreds to zero.

Preferably the intermediate wheel is received on the second axis of the counter chassis. The axes of the counter chassis are spaced apart by a distance slightly less than the combination of the tens and/or units wheel radius and the intermediate wheel radius. Thus when placed on the axes the first and second count wheels are aligned for engagement with the intermediate, wheel, providing a compact but accurately aligned and reliable counter display mechanism.

Preferably the counter chassis is configured to receive, and preferably guide motion of, the translating member. For example, protruding tabs on at least one or more preferably two opposed edges of the translating member are received in suitably configured channels of the counter chassis, thus enabling linear movement of the translating member as the tabs run in the channels, but preventing the translating member being pulled away from the counter chassis. Preferably the translating member further comprises a guiding slot, which runs substantially parallel to the direction of linear motion of the translating member when moving in the counting/resetting direction. Preferably the counter chassis further comprises a guiding protrusion that fits into the guiding slot and allows the translating member to move linearly but prevents movement laterally. Preferably the guiding protrusion is integrally formed with a protruding component of the counter chassis, for example the guiding protrusion is preferably an extension of one of the first or second axes of the counter chassis. Thus reliable linear and undeviating motion of the translating member is provided.

In preferred embodiments, the counter chassis further comprises a chassis pawl that is preferably integrally formed with the chassis. The chassis pawl is configured to enable the count wheels to rotate freely in the desired direction but to prevent backwards rotation of at least the first count wheel. This ensures that as the count of the counter is decremented (in embodiments where the number of remaining doses is displayed by the dose counting Mechanism) it is not possible for the Wheel to be rotated in the other direction, i.e. for the count to be incremented. This might otherwise occur during resetting of the counting mechanism for the next count, for example as the translating member and integrally formed pawl move back into the initial position (i.e. move in the resetting direction), or may occur accidentally, for example if the inhaler receives an impact from being dropped or the like. In a particularly preferred embodiment, the first count wheel comprises a plurality of counter-rotation teeth, each tooth preferably having a convex back icy surface. As the first count wheel rotates during counting, the pawl is deflected along the convex back surface of a counter-rotation tooth and the wheel is able to rotate in a first, forward direction. However the counter-rotation teeth further comprise an angular portion into which the chassis pawl head is received (e.g. snaps into after the pawl elastically returns to its undeflected position) after a unit count has been achieved. If there is subsequently any bias to rotate the first count wheel in a second, backward direction, abutment of the pawl head against the inner surface of the angular portion prevents movement of the first count wheel in this direction. In particularly preferred embodiments the angular portion and pawl head are configured such that bias to rotate the first count wheel in the backward direction increases the engagement between the pawl head and the angular portion. For example the pawl head and angular portion are preferably configured such that when abutting and pushed together, the pawl flexes inwardly towards the angular portion.

As discussed above, the second-count wheel is arranged to rotate when the intermediate wheel, with which it engages, rotates. In preferred embodiments, the second count wheel comprises a plurality of annularly spaced teeth about an outer periphery thereof, with notches between the teeth for receiving a tooth of the intermediate wheel, thus effecting relative rotation. In some embodiments the second count wheel has evenly and regularly spaced teeth around the entire outer periphery. However in particularly preferred embodiments there is provided a portion of the outer periphery of the second count wheel in which there are no teeth and corresponding notches or recesses present. In this manner when the second count wheel, has rotated relative to the intermediate wheel such that the portion with no teeth aligns with a tooth of the intermediate wheel, the intermediate wheel can no longer effect rotation of the second count wheel (since the rotating teeth of the intermediate wheel have no recesses to engage or teeth to push against). Thus subsequent rotation of the intermediate wheel has no effect at all on the second count wheel and this wheel is effectively permanently immobilised. This is particularly advantageous when the second count wheel, has been incremented down to the last count. Thus an end of life indicating mechanism is provided as the user will see that further actuations of the inhaler are not counted by the counter.

In preferred embodiments, the translating member further comprises at least one protrusion, which protrudes from a face of the translating member toward the first count wheel and is configured to engage at least a portion of the first count wheel in certain configurations and to prevent over-rotation of the first count wheel (and thus prevent overcounting, i.e. the first count wheel turning by more than the desired increment). This is particularly advantageous because the forces required to dispense a dose of medicament from the inhaler are relatively large and by associating counting with dispensing it is possible that such force may affect the counting mechanism. For example, in a preferred embodiment, movement of the dispensing mechanism on actuation is affected by a force of approximately 50 N, from a compressed spring or the like. Preferably a component of the dispensing mechanism that moves as the dose is dispensed pushes, pulls or otherwise actuates the translating member in its linear dispensing direction. The large spring force may cause the translating member to be pushed rapidly in the dispensing direction, typically at a velocity of about 4 ms$^{-1}$. The first count wheel, being rotated by the translating pawl moving at such a high velocity, could freely spin or at least would likely rotate beyond the desired increment, thus overcounting the dispensed dose. Preferably, therefore, the overcount preventing protrusion of the translating member comprises a linear protrusion for engagement with a plurality of spaced ribs protruding from an outer face of the first count wheel. As the translating member moves linearly and causes the first count wheel to rotate, the first overcount preventing protrusion also moves linearly (at the same speed as the pawl) and becomes located between a first (leading) rib and a second (following) rib of the first count wheel. The ribs and protrusion are configured such that the protrusion abuts the second (following) rib as the first count wheel reaches the end of its desired increment. The first overcount preventing protrusion thus blocks the first count wheel from rotating any further and thus prevents the first count wheel counting, beyond one dose. As the translating member returns to its initial position (i.e. moves linearly in the resetting direction), the first overcount preventing protrusion also moves linearly back to its initial position and is withdrawn from abutment with the rib of the first count wheel, thus freeing the count wheel to turn again on the next actuation.

Preferably the translating Member further or alternatively comprises a further protrusion which protrudes from the same face of the translating member (toward the first count wheel) as the overcount preventing protrusion. The further protrusion prevents counting when the counter is in the rest position and this rest count preventing protrusion is configured to engage at least a portion of the first count wheel when the counting mechanism is at rest. The rest count preventing protrusion is preferably configured to engage the same ribs of the first count wheel as the overcount preventing protrusion, but only when the translating member is in its initial, rest position (i.e. before the translating member has begun its motion in the counting direction, whereas the overcount preventing protrusion engages the ribs of the first count wheel after the translating member has completed its motion in the counting direction). The rest count preventing protrusion is preferably also a linear protrusion like the overcount preventing protrusion.

As discussed above, the dose counting mechanism comprises a counter and is preferably configured to display, inter alia, the number of doses of medicament remaining in the inhaler, or the number of doses of medicament that have been dispensed from the inhaler, etc. In preferred embodiments, the dose counting mechanism is substantially contained within the inhaler such that if is not accessible to the patient and cannot be removed from the inhaler. This prevents the dose counting mechanism being removed or otherwise tampered with and ensures that the count or other display of the dose counting mechanism is reliable and is directly associated with the amount of medicament in the inhaler.

However it is of course essential that at least the display of the dose counting mechanism is visible to the patient. Preferably the dose counting mechanism is contained within the inhaler, preferably behind a front fascia thereof, but the fascia comprises an aperture or window through which the display of the dose counting mechanism is visible. The aperture is preferably suitably sized and shaped that the display of the dose counting mechanism is clearly visible, but is not so large that the dose counting mechanism can be accessed or removed through the aperture.

Although the display of the dose counting mechanism is visible to the patient through the aperture in the above embodiments, it is particularly preferred that the patient cannot directly access or touch the display. Furthermore it is also preferable for the display to be covered to prevent ingress of foreign matter such as dirt or the like, which might interfere with operation of the dose counting mechanism and for safety ingress of foreign particles through the aperture and to other inhaler components should also be minimised.

Therefore in particularly preferred embodiments of the present invention, there is provided a cover or window, comprising a substantially transparent material, between the dose counting mechanism and the aperture. The window may comprise means for forming an air and/or moisture tight seal with the aperture, however this is not essential and it is only necessary for the window to provide a barrier to ingress of foreign particles into the dose counting mechanism. The window may be a separately provided component, or it may be integrally formed with the fascia. Preferably, however, the window comprises a component of the dose counting mechanism and more preferably, the window is integrally formed with a component of the dose counting mechanism, preferably with the counter chassis. The counter chassis is thus preferably entirely formed of a suitable transparent plastic, such as an amorphous copolymer like Eastman Tritan TX2001. The window may therefore comprise the portion of the counter chassis that lines up with the fascia aperture and may not be a distinct part of the counter chassis. Preferably, however, the window, though integrally formed with the counter chassis, is also a specifically configured part of the counter chassis. In a particularly preferred embodiment, the window is curved and protrudes from the counter chassis and preferably is suitably configured to magnify the display of the dose counting mechanism. Preferably the window is further configured such that, although the display is magnified by the window, the display is not significantly distorted. Such an arrangement is advantageously provided by a window having a level of magnification that is greater in one dimension than in a second, substantially perpendicular dimension. For example, if the window is rectangular and is wider (when the inhaler is held upright and in a position in which the display is intended to be read) than it is tall, preferably the magnification across the width of the window (i.e. in the x direction) is lower than the magnification across the height of the window (i.e. in the y direction). In preferred embodiments, the magnification in the x direction magnifies the size of the display by between about 0 and 30%, preferably between about 5 and 20%, more preferably is about 10%, and the magnification in the y direction magnifies the size of the display by between about 0 and 50%, preferably between about 10 and 30%, more preferably is about 20% and in any event is greater than the magnification in the x direction. This is preferably the case even for non rectangular (e.g. substantially square) windows. In a particularly preferred embodiment, the magnification in the x direction magnifies the size of the display by about 10% and in the y direction by about 20%. Such arrangements provide a window that very effectively allows sufficient light into the display to enable any digits or indicia, etc., to be clearly visible, and also magnifies the digits effectively but without significant distortion thereof, particularly sideways distortion (i.e. in the x direction which has a lower magnification). Such a window enhances the readability of the display considerably compared with either a flat window or a window with the same level of magnification along both axes.

The above dose counting mechanism and window for displaying the display of the counter of the dose counting mechanism provides an inhaler display that is significantly improved compared with known inhaler displays. Accordingly, from a further broad aspect of the present invention, there is provided an inhaler for delivery of a medicament by inhalation, the inhaler comprising:

a dispensing mechanism configured, on actuation, to dispense a dose of medicament, a dose counting mechanism comprising a counter for displaying indicia relating to the number of doses of medicament of the inhaler, and a window substantially aligned with the counter such that the indicia are viewable therethrough, wherein:

the window comprises a magnifying outer surface for magnifying the indicia of the counter, the magnification in a first dimension being greater than the magnification in a second dimension that is substantially perpendicular to the first dimension.

Preferably the window comprises a curved surface to provide the magnification, the curvature of the surface in the first dimension being greater than the curvature of the surface in the second direction. In a preferred embodiment where the window is rectangular and is wider (when the inhaler is held upright and in a position in which the display is intended to be read) than it is tall, preferably the magnification across the width of the window (i.e. in the x direction) is lower than the magnification across the height of the window (i.e. in the y direction). Preferably the magnification in the x direction magnifies the size of the display by between about 0 and 30%, preferably between about 5 and 20%, more-preferably is about 10%, and the magnification in the y direction magnifies the size of the display by between about 0 and 50%, preferably between about 10 and 30%, more preferably is about 20% and in any event is greater than the magnification in the x direction. This is preferably the case even for non rectangular (e.g. substantially square) windows. In a particularly preferred embodiment, the magnification in the x direction magnifies the size of the display by about 10% and in the y direction by about 20%.

It is clearly within the scope of the present invention, in embodiments therefore, that the window of this aspect of the present invention can be combined with any inhaler of the embodiments of the first aspect of the present invention. Namely a combination of any one or more of the essential and/or preferred features of the first broad aspect is envisaged as an embodiment of the present broad aspect. Some such combinations are specifically defined by the claims but others are entirely within the scope of the invention. Further preferred features of the inhalers in accordance with embodiments of either aspects of the present invention are described below.

In particularly preferred embodiments, the inhaler further comprises a resetting member configured for movement between a first position and a second position on application of a resetting force, and the dispensing mechanism comprising a loading member. The inhaler preferably further comprises a prevention mechanism comprising at least a first engaging member and a second engaging member, the first engaging member configured to engage in a mating configuration with the second engaging member, wherein when movement of the resetting member in the first direction is reversed before the resetting member reaches the second position, the first and second engaging members engage and hold the load of the loading member, thereby preventing actuation of the dispensing mechanism, until the resetting member is moved again in the first direction. At least one of the first and second engaging members is configured to resiliently flex, under load, into abutment with a substantially rigid component of the inhaler.

Thus there is provided an improved inhaler for dispensing one or more doses of medicament to a patient, that will not dispense a subsequent dose until the dispensing mechanism of the inhaler is fully reset. Such an arrangement provides an inhaler capable of dispensing a more reliable and consistent dose of medicament, as the dispensing mechanism will not fire until fully reset, which is the optimum initial state for dose dispensing. Furthermore, if actuation of the dispensing mechanism is prevented until the mechanism is fully reset, activation of the dose counting mechanism is optimised as the dispensing mechanism is configured to adjust the counter of the dose counting mechanism on actuation from a fully reset state. This reduces or eliminates the risk that the dispensing mechanism could fire and dispense a dose from a partially reset configuration whilst not adjusting the counter of the dose counting mechanism. Thus by ensuring the dispensing mechanism is fully reset before enabling a further medicament dose to be dispensed, activation of the dose counting mechanism should also be reliably performed and the counter should accurately reflect the number of actual doses dispensed from (or remaining in) the inhaler.

Preferably the inhaler further comprises a canister containing a medicament, the medicament preferably comprising at least one active pharmaceutical ingredient (API) and preferably also a propellant. It a particularly preferred embodiment, the medicament comprises at least a first active pharmaceutical ingredient and a second active pharmaceutical ingredient and a propellant. Preferably the medicament comprises a combination of a first active pharmaceutical ingredient and a second active pharmaceutical ingredient of the specific active ingredients listed in (i) to (xxi) herein below. In other preferred embodiments, the medicament comprises two or more of the specific active ingredients listed in (i) to (xxi) herein below. In preferred embodiments, particularly with such combinations of APIs, the medicament also comprises a propellant, preferably HFA 227 (1,1,1,2,3,3,3-heptafluoropropane) or HFA 134a (1,1,1,2,-tetrafluoroethane) or any other suitable propellant.

Preferably the loading member comprises a mechanism for applying compressive force to another component of the inhaler. In preferred embodiments in which the inhaler comprises a canister containing a medicament, the loading member preferably applies a compressive force to the canister. Preferably the compressive force compresses the canister against a retaining member that holds a nozzle of a metering valve of the canister in place (e.g. a nozzle block or a component of a mouthpiece of the inhaler). Compression of the canister opens the metering valve and causes a dose of medicament to be dispensed through the nozzle into the mouthpiece for inhalation by a patient.

In preferred embodiments, the loading member comprises a spring. In a compressed state, the spring stores a force that is at least sufficient to compress a canister against its valve nozzle and thus to dispense a metered dose of the medicament stored in the canister and preferably is also sufficient to actuate the dose counting mechanism. Typically for a pMDI the force applied to the canister by the loading member is in the order of about 50 N. Alternatively the loading member comprises any suitable means for compressing a canister, such as a compressed air mechanism or the like.

Preferably the dispensing mechanism comprises a releasable locking arrangement for locking the dispensing mechanism, for example by restraining the load of the loading member, until it is desired to actuate the dispensing mechanism, e.g., by releasing the loading member to compress a canister of the inhaler to dispense a dose of medicament. The releasable locking arrangement may have any suitable configuration for locking the dispensing mechanism that is releasable to enable a dose of medicament to be dispensed.

In particularly preferred embodiments, the releasable locking arrangement comprises a latch mechanism, preferably comprising a drop link for holding a lock member in position, the lock member in turn locking a lever arm in place. The lever arm is biased for rotation by the loading member (e.g. a compressed spring, in the loaded configuration) but is held against rotation by the lock member. Movement of the drop link releases the lock member which in turn releases the lever arm to rotate, thereby allowing the loading member to unload (e.g. the spring to expand) and to compress a canister to dispense a dose of medicament.

In accordance with embodiments of the present invention, on actuation of the inhaler, the dispensing mechanism moves the translating member in a substantially linear direction, whereby the pawl rotates the first count wheel. The dispensing mechanism preferably comprises a component that engages with the translating member, at least in certain configurations, and movement of the component of the dispensing mechanism during actuation subsequently moves the translating member. In embodiments comprising a releasable locking arrangement, the component of the dispensing mechanism that moves the translating member is preferably an integral part of the lever. Thus a multifunction lever is provided and the counting of a dose is directly related to the mechanism for dispensing a dose of medicament. Preferably the lever comprises an engaging protrusion, or more preferably a pair of engaging protrusions that engage with one or more notches on a back face of the translating member. As the lever pivots, the engaging protrusion(s) push downwards on the inner surface(s) of the notch(es) and thereby push the translating member linearly downwards to effect actuation of the counting mechanism.

In embodiments of the invention comprising a releasable locking arrangement, the drop link preferably moves in response to actuation by a user of the inhaler. Actuation of the inhaler may be by manual means, for example by means of an actuation member such as a button or lever, or the inhaler may be breath actuated. Particularly preferred inhalers in accordance with the present invention comprise both breath actuation means and manual actuation means so that a patient can choose how to actuate the inhaler (or can, for example, test the inhaler by dispensing a dose to ensure it is properly functioning, or can so manually prime the inhaler for example after periods Where the inhaler has not been used, or after it has been dropped etc.). Preferably the manual actuation means acts directly on a the component of the breath actuation means that moves in response to patient inhalation (e.g. the manual actuation means acts directly on a vane of the breath actuation means, preferably the manual actuation means, pushes the vane and simulates patient inhalation).

In a particularly-preferred embodiment of the present invention, the inhaler comprises a drop link for holding a lock member in position, the lock member in turn locking a lever arm in place as discussed above. The drop link is preferably retained in the locking position by a breath-triggered member, preferably a vane that pivots in response to a pressure drop within the inhaler airflow passage, such pressure drop occurring as a patient inhales through a mouthpiece of the inhaler. Thus the releasable locking arrangement holds the load of a loading member, e.g. a compressed spring, until a patient inhales through the mouthpiece to cause the releasable locking arrangement to release the load of the spring, thereby compressing a canister of the inhaler to dispense a dose of medicament.

Further details of a breath actuated inhaler arrangement are described in WO2008/082359 and such an arrangement is compatible with the inhaler of embodiments of the present invention.

As discussed above, the inhaler preferably comprises a resetting member. The resetting member resets the inhaler after it has been used, by reloading the loading member of the dispensing mechanism, thus enabling the dispensing mechanism to be actuated again and a further dose to be dispensed.

Preferably the resetting member comprises a manually actuatable component of the inhaler. This enables a user of the inhaler to reset the dispensing mechanism after a dose has been dispensed, arming the inhaler for dispensing further doses as required. In particularly preferred embodiments, the resetting member comprises a rotatable member of the inhaler, preferably a cap of the inhaler which also servers to cover and protect a mouthpiece of the inhaler when in a closed position. Such an arrangement is particularly advantageous because it encourages a patient to close the inhaler cap immediately after use, thus priming the device and resetting it to its preferred rest configuration, as well as protecting the mouthpiece from ingress of dirt or dust, etc. Alternatively or preferably additionally, the cap also prevents actuation of the inhaler when in the closed position, thus preventing accidental actuation of the inhaler. Preferably the cap holds or otherwise prevents movement of certain components of the inhaler and prevents breath and/or manual actuation of the inhaler until it is opened, preferably by abutment with the components.

In particularly preferred embodiments, the resetting member comprises a cap that pivots about an axis between a first position and a second position. Pivoting of the cap about its axis is effected by a patient applying a resetting force to rotate the cap. In the first position, the cap is rotated away from the mouthpiece leaving it free for a patient to insert into their mouth for inhalation. In a particularly preferred embodiment, the cap is locked into the first, open position, for example by a snap fit or friction fit between a portion of the cap and a portion of the inhaler when in the open position. The snap fit or friction fit is configured to be sufficient to hold the cap in the desired open position, but is also sufficiently weak so that it can be readily overcome, and the cap displaced, by a typical user of the inhaler.

Applying a resetting force to the resetting member moves the resetting member from a first position to a second position. Preferably, in the embodiment where the resetting member comprises a cap, in the second position the cap covers, and preferably in co-operation with the inhaler body and other components, fully encloses a mouthpiece of the inhaler, thereby protecting the mouthpiece when the inhaler is not in use.

The resetting member is configured to move in a first direction from a first position to a second position and to load the loading member as it moves in the first direction. Preferably, in the embodiment where the resetting member comprises a cap, rotation of the cap causes translational movement of a component of the dispensing mechanism, preferably a yoke substantially aligned along a main axis of the inhaler body. The translation movement of the component, for example the yoke, acts to compress the loading member and thus to load the loading member and reset the dispensing mechanism.

In a particularly preferred embodiment, the cap rotates and pushes upwards on a yoke that compresses a spring against a top portion of the inhaler, thus loading the so dispensing mechanism. Preferably a releasable locking arrangement is armed when the cap has substantially fully rotated (and the yoke has translated the desired amount and thus compressed the spring to the desired load) to lock the dispensing mechanism until the patient next actuates the inhaler to dispense a dose of medicament. Preferably the cap when in the closed position prevents downward movement of the yoke and thereby helps to prevent the inhaler from being actuated when the cap is closed.

As discussed above, the resetting member of the inhaler is configured for movement between a first position and a second position on application of a resetting force, the movement from the first position to the second position loading the loading member and resetting the dispensing mechanism. In any position between the first and second positions, i.e. in an intermediate position, the dispensing mechanism may only be partially reset, which may adversely affect the next dispensed dose and/or cause inaccuracies in the dose count of the counter, if the inhaler is actuated from the intermediate position. For example, in the intermediate position, if the canister is not frilly released from compression by the load of the loading Member, the valve of the canister may not refill sufficiently or at all and any subsequent dose may be of a lower dose weight than desired.

Still further, in preferred embodiments, for example inhalers comprising a releasable locking arrangement, in the intermediate position the releasable locking arrangement may not be fully engaged and thus unable to hold the load of the loading member. If the patient releases the resetting member when in the intermediate position (i.e. before the dispensing mechanism is fully reset), the releasable locking arrangement may be ineffective and any load applied to the loading member may be released to compress the canister again. This may cause a full or a low dose of medicament to be released, but the dose may not be registered by the dose counting mechanism if the inhaler was not reset beyond a position at which the counting mechanism is reset for further counting. In other words, if the inhaler is only partially reset, it may not be far enough to enable resetting of the dose counting mechanism, thereby allowing a dose (albeit possibly not a full weight dose) to be dispensed but not counted.

Therefore in preferred embodiments of the present invention, the inhaler comprises a prevention mechanism for preventing actuation of the dispensing mechanism in certain configurations. In particular, the prevention mechanism prevents actuation of the dispensing mechanism when the resetting member has been moved from the first position but has not fully reached the second position, i.e. is in an intermediate position therebetween. The prevention mechanism comprises at least a first engaging member and a second engaging member, the first engaging member configured to engage in a mating configuration with the second engaging member. The engaging members are configured to mutually engage if, during movement of the resetting member from the first position to the second position, movement is ceased and possibly reversed before the resetting member reaches the second position (i.e. if the user stops-moving the resetting member in the first direction before it is fully reset, and possibly the resetting member begins to move in the opposite, second direction).

The engaging members may engage indirectly with each other, i.e. via an intermediate component, but preferably the first engaging member directly engages with the second engaging member. After engagement, the engaging members hold the load of the loading member and at least one of the engaging members is configured to flex under this load and move into abutment with another, more rigid component of the inhaler. Thus the load that would otherwise be entirely absorbed by the engaging members is at least partially absorbed by the more rigid component of the inhaler against which at least one of the engaging members abuts. This is advantageous because the engaging members must be sufficiently flexible to permit engagement and disengagement and are relatively small components in order to ensure the inhaler weight and size is minimised. Absorbing the approximately 50 N force of a spring substantially entirely through the engagement members could cause the members to deform or break. Indeed, plastic creep has been observed in members formed of plastics that are typically used for such members. However in the embodiments of the present invention, a significant proportion of the load is absorbed in the compressive contact between at least one of the engaging members and the more rigid inhaler component, which latter component is better suited and configured to withstand such forces with substantially no detrimental impact on the component.

The engaging members are configured to engage with each other readily when movement in the first direction of the resetting member is reversed. Preferably the engaging members are further configured to disengage with each other readily when movement in the first direction of the resetting member is initiated again (for example by the user moving the resetting member further onward to the second position to reset the dispensing mechanism and to fully load the loading member). In particularly preferred embodiments comprising a releasable locking arrangement, the releasable locking arrangement is configured to engage and hold the load of the loading member when the inhaler is fully reset, i.e. when the resetting member has reached the second position. Prior to the resetting member reaching the second position, the prevention mechanism is configured to re-engage and hold the load of the loading member every time the direction of motion of the resetting member is reversed from the first direction, and to again disengage as motion in the first direction is resumed.

The first and second engaging members may be of any suitable configuration for mutually engaging and holding aloud. Preferably one of the first engaging member and the second engaging member comprises a female engaging portion and the respective other of the first engaging member and the second engaging member comprises a male engaging portion. In a preferred embodiment, the female engaging portion comprises a slot, notch or other recess for receiving a male engaging portion comprising a protrusion, hammer head, tooth or the like.

In another preferred embodiment, the first engaging member and the second engaging member each comprise a hook portion configured to engage with the hook portion of the respective other of the first engaging member and the second engaging member. Thus when engaged, the hook portions mutually co-operate to hold at least a proportion of the load of the loading member when under tension (i.e. when loaded). Other configurations of the engaging members are possible, for example a hook and eye configuration, a ball and socket arrangement or the like. Such male/female or hook arrangements are also readily disengagable as required when the load is relieved from the engaging members such that they are no longer pulled against each other, i.e. are no longer held under tension.

The first engaging member and the second engaging member are configured to engage in at least one mating configuration. For example in embodiments where the first engaging member comprises a first hook portion and the second engaging member comprises a second hook portion the mating configuration comprises engagement of the first hook portion with the second hook portion. In some embodiments however, the first engaging member and the second engaging, member are configured to engage in a plurality of mating configurations. For example the first engaging member preferably comprises at least two hook portions, preferably spaced apart along a length of the first engaging member. In this configuration, the first hook portion of the first engaging member can engage with the second hook portion of the Second engaging member at a first intermediate position of the resetting member, or the second hook portion of the first engaging member can engage with the second hook portion of the second engaging member if the resetting member is at a second intermediate position (e.g. is further advanced towards the second position but still has not reached this end position). Such a ratchet arrangement provides multiple positions of engagement of the engaging members enabling a greater number of intermediate positions of the resetting member to be accounted for if necessary.

Preferably the first and second engaging members engage in any suitable manner and in a particularly preferred embodiment, the first and second engaging members flex or snap into engagement.

As discussed above, at least one of the first and second engaging members is configured to resiliently flex, under load, into abutment with a substantially rigid component of the inhaler. In the preferred embodiment where one of the engaging members comprises a hook or hammer head, preferably at least this head portion of the engaging member is deflected as the member flexes and abuts another component of the inhaler. In this arrangement, although the head portion is partially under a tensile force across a narrower dimension, it is through compression of the head portion against the rigid component of the inhaler that much of the force is relieved, and this occurs through a wider dimensioned (and stronger) part of the head. Thus not only is a significant proportion of the force relieved from the weaker part of the engaging member, it is also absorbed by another component which can be configured to be stronger and more suitable for absorbing forces. Thus material creep, deformation and damage is substantially minimised or prevented and an improved arrangement is provided compared with, for example, the prior art blocking mechanisms discussed above.

The at least one of the first and second engaging members that is configured to resiliently flex, under load, into abutment with a substantially rigid component of the inhaler is also configured such that, when the load is removed from the engaging member, it flexes, back into substantially its original configuration. Namely the engaging member is elastic in this regard and does, not plastically or permanently deform to any significant extent.

As discussed above, the first and second engaging members engage in a mating configuration and at least one deflects into abutment with another component of the inhaler, to hold the load of the loading member, when motion of the resetting member is reversed from the first direction. Preferably the first engaging member is disengaged from the second engaging member in all other configurations, of inhaler. In particular, when the resetting member is in the first position (for example in embodiments Where the resetting member comprises a mouthpiece cap, when the cap is open to expose the mouthpiece) and the inhaler has not yet been fired (i.e. the inhaler is in the prefire or armed configuration) the first engaging member is spaced apart from the second engaging member such that they cannot engage. Preferably when the resetting member is in the second position (for example in embodiments where the resetting member comprises a mouthpiece cap, when the cap is closed and covering the mouthpiece) the first engaging member is spaced apart from the second engaging member such that they cannot engage. Preferably when the resetting member is in the intermediate position and is in motion in the first direction (i.e. when the patient is in the process of resetting the dispensing mechanism) the first engaging. Member does not engage with the second engaging member because they are spaced apart, relatively deflected or are otherwise incapable of engagement. This ensures that the engaging members do not engage (and therefore do not hold the load) in any configuration where this would be undesirable, for example when dispensing a dose or when properly resetting the dispensing mechanism. Thus the prevention mechanism does not interrupt proper and desired operation of the inhaler but only engages when undesired operation occurs, such as reverse movement of the resetting member before the inhaler is completely reset.

The engaging members of the prevention mechanism may be brought into mutual engagement and/or separated from mutual engagement by any suitable means. For example the engaging members may be moved in a linear direction towards each other for engagement and away from each other for disengagement, or by translation in any other direction, or by rotation of one or more of the engaging members, etc. Preferably, in configurations where the first engaging member may need to translate, rotate or otherwise move entirely past the second engaging member, at least one of the engaging members is configured to be deflectable relative to the other, as discussed below.

In preferred embodiments at least one of the engaging members of the prevention mechanism is formed integrally with, or is a component of, another component of the inhaler. Preferably the first engaging member is formed integrally with, or is a component of a first component of the inhaler, and the second engaging member is formed integrally with, or is a component of a second component of the inhaler. In particularly preferred embodiments, the first and second components of the inhaler are separately formed components which move relative to each other as part of at least one function of the inhaler. Furthermore, in preferred embodiments the substantially rigid component of the inhaler into abutment with which at least one of the engaging, members moves under load, is also formed integrally with, or is a component of another component of the inhaler. In particularly preferred embodiments, the substantially rigid component and the engaging member which is configured to abut the substantially rigid component are integrally formed with, or component parts of, the same component, and preferably are both integral components of a chassis of the inhaler as discussed further below.

In particularly preferred embodiments of the invention, comprising a releasable locking arrangement as discussed above, the first engaging member is preferably formed as an integral part of a lever of the releasable locking arrangement. Preferably the lever moves, preferably in a pivoting motion, as the load of the loading member is released to dispense a dose and the integrally formed first engaging member also moves as a component part of the lever. Preferably the inhaler further comprises a chassis, the chassis housing many of the components and mechanisms of the inhaler and preferably at least partially defining an airflow passage through the inhaler from a mouthpiece. Preferably the second engaging member is formed as an integral part of the chassis, preferably as an upstanding member that is in the proximity of the lever and the first engaging member when the inhaler components are assembled in the chassis. In further embodiments, only one or the other of the engagement members may be integrally formed as a part of another component of the inhaler, with the other of the engagement members being formed as a separate component. In particularly preferred embodiments, the dose counting mechanism is configured as a separately provided unit which snap fits into the inhaler chassis in an appropriate position for actuation by the dispensing mechanism. Whilst the inhaler may be configured to receive only a single type of counter, in alternative embodiments, the inhaler is configured to receive a plurality of different types of counters. For example, a single inhaler may be capable of receiving a mechanical counter or an electronic counter or even a dummy counter (e.g. a face plate or the like if no counter is required). An inhaler having interchangeable counter mechanisms may be advantageous for users having different requirements of the device.

In preferred embodiments of the present invention, the prevention mechanism comprises at least one first engaging member and at least one second engaging member, the engaging members configured to engage with each other in a mating configuration. In preferred embodiments, a plurality of pairs of engaging members is provided, thus providing a robust prevention mechanism with multiple members for mutual engagement. In a particularly preferred embodiment, in which the first engaging member is a component or an integral part of a lever, there are at least two first engaging members, each of which engages in a mating configuration with a respective one of at least two second engaging members, preferably that are components or integral parts of a chassis.

The first engaging member of the lever and the second engaging member of the chassis in embodiments of the present invention have the following relative positions depending on the configuration of the inhaler. When the resetting member is in the second position (e.g. the cap is closed in embodiments having a mouthpiece cap), the first engaging member overlaps with, but is preferably displaced away from the second engaging member so that they are not in a mating configuration. To use the inhaler, a patient moves the resetting member towards the first position (e.g. opens the cap). In preferred embodiments wherein the dispensing mechanism comprises a yoke, the cap is configured to release the yoke when opened. The yoke moves downwards slightly under the load of the loading member (a compressed spring in preferred embodiments), until the releasable locking mechanism is fully engaged. The downward yoke movement pivots the lever. Thus the first engaging member moves towards the second engaging member but preferably still does not engage the second engaging member. When the patient inhales, or otherwise actuates the inhaler to dispense a dose of medicament, the releasable locking mechanism releases the dispensing mechanism and the load in the loading member is freed and compresses a canister of the inhaler, preferably via the yoke which is pushed downwards onto the canister base. The yoke rotates the lever and at least the engaging portion of the first engaging member must pass beyond the engaging portion of the second engaging member without the two engaging portions mating. In preferred embodiments, at least one of the first engaging member and the second engaging member is configured to be sufficiently flexible such that at least the engaging portion of the flexible engaging member can deflect or otherwise flex away from the other engaging member to allow the engaging members to pass without mating. In some embodiments, both engaging members are flexible and may mutually deflect each other. In any of these embodiments, the shape of the engaging portion of one or both of the first and second engaging members may be configured to aid deflection. For example, in preferred embodiments, at least one of the engaging portions comprises a sloped deflecting edge to aid deflection of the other of the engaging portions. At least one of the engaging portions preferably additionally or alternatively comprises a flat portion to aid deflection and relative travel past of the other of the engaging portions. In a preferred embodiment, the flexible member is biased to pass down one side of the other engaging portion (during firing) and is deflected to run up the other side of the other engaging portion upon return.

Thus the prevention mechanism allows (i.e. docs not interfere with) operation of the inhaler in the desired manner. Namely the First and second engaging members do not engage in the muting configuration during opening of the inhaler cap or during dispensing of a dose of medicament. Rather the first and second engaging members are configured to deflect to allow translational movement in a first direct, hereinafter referred to as the dispensing direction, during dispensing of a dose of medicament.

After a dose is dispensed, the dispensing mechanism of the inhaler must be fully reset in order to ensure the next dispensed dose is of the correct volume and dose weight and is accurately and reliably counted by the dose counting mechanism. In preferred embodiments, resetting of the dispensing mechanism is achieved by applying a resetting force to rotate the mouthpiece cap, thus pushing upwards on the yoke and reloading the spring. When the spring is fully loaded, which is when the cap is fully closed (i.e. moved to the second position) the dispensing mechanism is prevented from being actuated, either by the lever of the releasable locking arrangement being locked or by the closed cap preventing downward movement of the yoke, or a combination of these. However when the cap is not fully closed, this is not the ease and it is possible the dispensing mechanism could at least partially re-fire. To prevent this, the prevention mechanism is configured to engage as required in such intermediate positions. Namely, as the cap is initially moved away from the first (open) position and the yoke begins to move in the opposite direction to the dispensing direction, hereinafter referred to as the resetting direction, the lever rotates and the first engaging member moves towards the second engaging member to a position where it is capable of engagement in u mating configuration therewith. In preferred embodiments, at least one of the engaging portions of the first or second engaging members is configured to be deflected during relative positioning of the engaging members.

If the cap is not fully closed whilst the engaging members are in this configuration and instead begins to move in the opening direction, then the yoke moves back in the dispensing direction thus rotating the lever and engaging the engaging members in the mating configuration. The mutually engaged engaging members are pulled under the spring loud which attempts to pull the engaging members apart and causes the at least one of the first and second engaging members that is configured to resiliently flex under load, to flex and move into the position where it abuts a substantially rigid component of the inhaler. This rigid and strong arrangement is easily capable of holding tire loud of the loading member without significantly deforming or otherwise damaging the engaging members or causing plastic creep of the components even through repeated engagements.

In this manner the engaging members are configured not to allow movement in the dispensing direction until movement of the resetting member is continued and completed, and the first engaging member is fully displaced back to the reset position of the lever. In preferred embodiments, the First engaging member is moved to a non-engaging position relative to the second engaging member by deflecting one relative to the other and thus out of the possible mating configuration. At the end of the resetting operation, i.e. when the lever reaches a position in which the releasable locking arrangement will lock the lever in place und/or the when the fully closed cap locks the yoke, the First and second engaging members will be at rest and cannot engage Other configurations are possible but the basic principle of the interactions between the engagement members remains the same.

Thus a reliable and improved mechanism is provided for ensuring that the dispensing mechanism, which controls dispensing of doses of medicament and counting thereof, is fully reset after each dose is dispensed, thus ensuring reliable dosing and counting of the doses. In the event that the dispensing mechanism is only partially reset, the prevention mechanism engages to prevent the dispensing force of the loading member from dispensing a further, low weight and potentially uncounted dose, until the mechanism is fully reset. The prevention mechanism allows motion of the component parts of the inhaler during dispensing in the dispensing direction but prevents motion in the dispensing direction once engaged until the engagement is overridden by fully completing the resetting operation. The first and second engaging members of the prevention mechanism mutually engage and remain under tension and compression against a rigid component of the inhaler to hold the dispensing mechanism and to prevent further movement in the dispensing direction. Once the tension is released, the first and second engaging members may be displaced upon fully resetting the dispensing mechanism or may re-engage if the dispensing mechanism is still not fully reset. This is in contrast to the prior art system disclosed in WO2004/041334 for example, which discloses a blocking mechanism in a manually actuatable inhaler where the components that block movement are held under a direct compressive force, as shown in FIG. 20. The compressive force arrangement may be less reliable and resilient as the components may be difficult to configure such that they are strong enough to resist material creep and deformation over time and use, but flexible enough to reliably engage and disengage with repeated uses and over a long period of lime.

It should be noted that in this application the relative terms such as "upper", "lower", "above", "below", "upright", etc., have been used for explanatory purposes to describe the internal relationship between elements of the inhaler, regardless of how the inhaler is oriented in the surrounding environment. Furthermore references to interactions between components of the inhaler in this application, such as "abutting", "applying", "compressing", etc., are intended to cover direct and indirect interactions (indirect interactions being those with one or more other components between the interacting components and direct interactions being those where the interacting components are in direct contact with no intervening components).

The medicament in the inhaler may contain various active ingredients. The active ingredient may be selected from any therapeutic or diagnostic agent. For example, the active ingredient may be an antiallergic, a bronchodilator (e.g. a beta2-adrenoceptor agonist or a muscarinic antagonist), a bronchoconstrictor, a pulmonary lung surfactant, an analgesic, an antibiotic, a mast cell inhibitor, an antihistamine, an anti-inflammatory, an antineoplastic, an anaesthetic, an antitubercular, an imaging agent, a cardiovascular agent, an enzyme, a steroid, genetic material, a viral vector, an antisense agent, a protein, a peptide, a non-steroidal glucocorticoid Receptor (GR Receptor) agonist, an antioxidant, a chemokine antagonist (e.g. a CCR1 antagonist), a corticosteroid, a CRTh2 antagonist, a DP1 antagonist, an Histone Deacetylase Inducer, an IKK2 inhibitor, a COX inhibitor, a lipoxygenase inhibitor, a leukotriene receptor antagonist, an MPO inhibitor, a p38 inhibitor, a PDE inhibitor, a PPARγ agonist, a protease inhibitor, a statin, a thromboxane antagonist, a vasodilator, an ENAC blocker (Epithelial Sodium-channel blocker) and combinations thereof.

Examples of specific active ingredients that can be incorporated in the inhaler include:
(i) antioxidants:—Allopurinol, Erdosteine, Mannitol, N-acetyl cysteine choline ester, N-acetyl cysteine ethyl ester, N-Acetylcysteine, N-Acetylcysteine amide and Niacin;
(ii) chemokine antagonists:—BX471 ((2R)-1-[[2-[(aminocarbonyl)amino]-4-chlorophenoxy]acetyl]-4-[(4-fluorophenyl)methyl]2-methylpiperazine monohydrochloride), CCX634, N-{2-[((2S)-3-{[1-(4-chlorobenzyl)piperidin-4-yl]amino}-2-hydroxy-2-methylpropyl)oxy]-4-hydroxyphenyl}acetamide (see WO 2003/051839), and 2-{2-Chloro-5-{[(2S)-3-(5- chloro-1'H,3H-spiro[1-benzofuran-2,4'-piperidin]-1'-yl)-2-hydroxypropyl]oxy}-4-[(methylamino)carbonyl]phenoxy}-2-methylpropanoic acid-(see WO 2008/010765), 656933 (N-(2-bromophenol)-N-(4-cyano-1H-1,2,3-benzotriazol-7-yl)urea), 766994 (4-({[({[(2R)-4-(3,4-dichlorobenzyl)morpholin-2-yl]methyl}amino)carbonyl]-amino}methyl)benzamide), CCX-282, CCX-915, Cyanovirin N, E-921, INCB-003284, INCB-9471, Maraviroc, MLN-3701, MLN-3897, T-487 (N-{1-[3-(4-ethoxyphenyl)-4-oxo-3,4-dihydropyrido[2,3-d]pyrimidin-2-yl]ethyl}-N-(pyridin-3-ylmethyl)-2-[4-(trifluoromethoxy)phenyl]acetamide) and Vicriviroc (iii) Corticosteroids:—Alclometasone dipropionate, Amelometasone, Beclomethasone dipropionate, Budesonide, Butixocort propionate, Ciclesonide, Clobetasol propionate, Desisobutyrylciclesonide, Etiprednol dicloacetate, Fluocinolone acetonide, Fluticasone Furoate, Fluticasone propionate, Loteprednol etabonate (topical) and Mometasone furoate.

(iv) DP1 antagonists:—L888839 and MK0525;

(v) Histone deacetylase inducers:—ADC4022, Aminophylline, a Methylxanthine or Theophylline;

(vi) IKK2 inhibitors:—2-{[2-(2-Methylamino-pyrimidin-4-yl)-1H-indole-5-carbonyl]-amino}-3-(phenyl-pyridin-2-yl-amino)-propionic acid;

(vii) COX inhibitors:—Celecoxib, Diclofenac sodium, Etodolac, Ibuprofen, Indomethacin, Meloxicam, Nimesulide, OC1768, OC2125, OC2184, OC499, OCD9101, Parecoxib sodium, Piccatannol, Piroxicam, Rofecoxib and Valdecoxib;

(viii) Lipoxygenase inhibitors:—Ajulemic acid, Darbufelone, Darbufelone mesilate, Dexibuprofen lysine (monohydrate), Etalocib sodium, Licofelone, Linazolast, Lonapalene, Masoprocol, MN-001, Tepoxalin, UCB-35440, Veliflapon, ZD-2138, ZD-4007 and Zileuton ((±)-1-(1-Benzo[b]thien-2-ylethyl)-1-hydroxyurea);

(ix) Leukotriene receptor antagonists:—Ablukast, Iralukast (COP 45715A), Montelukast, Montelukast sodium, Ontazolast, Pranlukast, Pranlukast hydrate (mono Na salt), Verlukast (MK-679) and Zafirlukast;

(x) MPO Inhibitors:—Hydroxamic acid derivative (N-(4-chloro-2-methyl-phenyl)-1-phenyl-4-[[(4-propan-2-ylphenyl)sulfonylamino]methyl]piperidine-1-carboxamide), Piccatannol and Resveratrol;

(xi) Beta2-adrenoceptor agonists:—metaprotcrenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol, indacatcrol, salmeterol (e.g. as xinafoate), bambuterol (e.g. as hydrochloride), carmoterol, indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide; 3-(4-{[6-({(2R)-2-hydroxy-2-[4-hydroxy-3-(hydroxy-methyl)phenyl]ethyl}amino)-hexyl]oxy}butyl)benzenesulfonamide; GSK 159797, GSK 159802, GSK 597901, GSK 642444, GSK 678007; and a compound selected from N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthypethoxy]propanamide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-chlorophenyl)ethoxy]propanamide, 7-[(1R)-2-({2-[(3-{[2-(2-Chlorophenyl)ethyl]amino}propyl)thio]ethyl}amino)-1-hydroxyethyl]-4-hydroxy-1,3-benzothiazol-2(3H)-one, and N-Cyclohexyl-N'-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. wherein the counter ion is hydrochloride (for example a monohydrochloride or a dihydrochloride), hydrobromide (for example a monohydrobromide or a dihydrobromide), fumarate, methanesulphonate, ethanesulphonate, benzenesulphonate, 2,5-dichlorobenzenesulphonate, p-toluenesulphonate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonic), D-mandelate, L-mandelate, cinnamate or benzoate.)

(xii) Muscarinic antagonists:—Aclidinium bromide, Glycopyrrolate (such as R,R-, R,S-, S,R-, or S,S-glycopyrronium bromide), Oxitropium bromide, Pirenzepine, telenzepine, Tiotropium bromide, 3(R)-1-phenethyl-3-(9H-xanthene-9-carbonyloxy)-1-azoniabicyclo[2.2.2]octane bromide, 3(R)-3-[(2S)-2-cyclopentyl-2-hydroxy-2-thien-2-ylacetoxy]-1-(2-phenoxyethyl)-1-azoniabicyclo[2.2.2]actane bromide, a quaternary salt (such as [2-((R)-Cyclohexyl-hydroxy-phenyl-methyl)-oxazol-5-ylmethy]-dimethyl-(3-phenoxy-propyl)-ammonium [2-(4-Chloro-benzyloxy)-ethyl]-[2-((R)-cyclohexyl-hydroxy-phenyl-methyl)-oxazol-5-ylmethyl]-dimethyl-ammonium salt and (R)-1-[2-(4-Fluorophenyl)-ethyl]-3-((S)-2-phenyl-2-piperidin-1-yl-propionyloxy)-1-azonia-bicyclo[2.2.2]octane salt wherein the counter-ion is, for example, chloride, bromide, sulfate, methanesulfonate, benzenesulfonate (besylate), toluenesulfonate (tosylate), napthalenebissulfonate (napadisylate or hemi-napadisylate), phosphate, acetate, citrate, lactate, tartrate, mesylate, maleate, fumarate or succinate)

(xiii) p38 Inhibitors:—681323, 856553, AMG548 (2-[[(2S)-2-amino-3-phenylpropyl]amino]-3-methyl-5-(2-naphthalenyl)-6-(4-pyridinyl)-4(3H)-pyrimidinone), Array-797, AZD6703, Doramapimod, KC-706, PH 797804, R1503, SC-80036, SCIO469, 6-chloro-5-[[(2S,5R)-4-[(4-fluorophenyl)methyl]-2,5-domethyl-1-piperazinyl]carbonyl]-N,N,1-trimethyl-α-oxo-1H-indole-3-acetamide, V X702 and VX745 (5-(2,6-dichlorophenyl)-2-(phenylthio)-6H-pyrimido[1,6-b]pyridazin-6-one);

(xiv) PDE Inhibitors:—256066, Arofylline (3-(4-chlorophenyl)-3,7-dihydro-1-propyl-1H-Purine-2,6-dione), AWD 12-281 (N-(3,5-dichloro-4-pyridinyl)-1-[(4-fluorophenyl)methyl]-5-hydroxy-α-oxo-1H-indole-3-acetamide), BAY19-8004 (Bayer), CDC-801 (Calgene), Celgene compound (((βR)-β-(3,4-dimethoxyphenyl)-1,3-dihydro-1-oxo-2H-isoindole-2-propanamide), Cilomilast (cis-4-cyano-[3-(cyclopentyloxy)-4-methoxyphenyl]-cyclohexanecarboxylic acid), 2-(3,5-dichloro-4-pyridinyl)-1-(7-methoxyspiro[1,3-benzodioxole-2,1'-cyclopentan]-4-yl)ethanone (CAS number 185406-34-2)), (2-(3,4-difluorophenoxy)-5-fluoro-N-[cis-4-[(2-hydroxy-5-methylbenzoyl)amino]cyclohexyl]-)-3-pyridinecarboxamide), (2-(3,4-difluorophenoxy)-5-fluoro-N-[cis-4-[[2-hydroxy-5-(hydroxymethyl)benzoyl]amino]cyclohexyl]-3-pyridinecarboxamide), CT2820, GPD-1116, Ibudilast, IC 485, KF 31334, KW-4490, Lirimilast ([2-(2,4-dichlorobenzoyl)-6-[(methylsulfonyl)oxy]-3-benzofuranyl]-urea), (N-cyclopropyl-1,4-dihydro-4-oxo-1-[3-(3-pyridinylethynyl)phenyl]-)-1,8-naphthyridine-3-carboxamide), (N-(3,5-dichloro-4-pyridinyl)-4-(difluoromethoxy)-8-[(methylsulfonyl)amino])-1-dibenzofurancarboxamide), ONO6126, ORG 20241 (4-(3,4-dimethoxyphenyl)-N-hydroxy-)-2-thiazolecarboximidamide), PD189659/PD168787 (Parke-Davis), Pentoxifylline (3,7-dihydro-3,7-dimethyl-1-(5-oxohexyl)-)-1H-purine-2,6-dione), compound (5-fluoro-N-[4-[(2-hydroxy-4-methyl-benzoyl)amino]cyclohexyl]-2-(thian-4-yloxy)pyridine-3-carboxamide), Piclamilast (3-(cyclopentyloxy)-N-(3,5-dichloro-4-pyridinyl)-4-methoxy-benzamide), PLX-369 (WO 2006026754), Roflumilast (3-(cyclopropylmethoxy)-N-(3,5-dichloro-4-pyridinyl)-4-(difluoromethoxy)benzamide), SCH 351591, (N-(3,5-dichloro-1-oxido-4-pyridinyl)-8-methoxy-2-(trifluoromethyl)-5-quinolinecarboxamide), SelCID™ CC-10004 (Calgene), T-440 (Tanabe), Tetomilast (6-[2-(3,4-diethoxyphenyl)-4-thiazolyl]-2-pyridinecarboxylic acid), Tofimilast (9-cyclopentyl-7-ethyl-6,9-dihydro-3-(2-thienyl)-5H-pyrazolo[3,4-c]-triazolo[4,3-a]pyridine), TPI 1160, UCB 101333-3 (N,2-dicyclopropyl-6-(hexahydro-1H-azepin-1-yl)-5-methyl-4-pyrimidinamine), V-11294A (Napp), VM554/VM565 (Yentas), and Zardaverine (6-[4-(difluoromethoxy)-3-methoxyphenyl]-3(2H)-pyridazinone).

(xv) PDE5 Inhibitors:—Gamma-glutamyl[s-(2-iodobenzyl)cysteinyl]glycine, Tadalafil, Vardenafil, sildenafil, 4-phenyl-methylamino-6-chloro-2-(1-imidazolyl)-quinazolino, 4-phenyl-methylamino-6-chroro-2-(3-pyridyl)-quinazoline, 1,3-dimethyl-6-(2-propoxy-5-Methanesulphonylamidophenyl)-1,5-dihydropyrazolo[3,4-d]pyrimidin-4-one and 1-cyclopentyl-3-ethyl-6-(3-ethoxy-4-pyridyl)-pyrazolo[3,4-d]pyrimidin-4-one;

(xvi) PPARγ agonists:—Pioglitazone, Pioglitazone hydrochloride, Rosiglitazone Maleate, Rosiglitazone Maleate ((−)-enantiomer, free base), Rosiglitazone maleate/Metformin hydrochloride and Tesaglitizar;

(xvii) Protease Inhibitors:—Alpha1-antitrypsin proteinase Inhibitor, EP1-HNE4, UT-77, ZD-0892, DPC-333, Sch-709156 and Doxycycline;

(xviii) Statins:—Atorvastatin, Lovastatin, Pravastatin, Rosuvastatin and Simvastatin (xix) Thromboxane Antagonists: Ramatroban and Seratrodast;

(xx) Vasodilators:—A-306552, Ambrisentan, Avosentan, BMS-248360, BMS-346567, BMS-465149, BMS-509701, Bosentan, BSF-302146 (Ambrisentan), Calcitonin Gene-related Peptide, Daglutril, Darusentan, Fandosentan potassium, Fasudil, Iloprost, KC-12615 (Daglutril), KC-12792 2AB (Daglutril) Liposomal treprostinil; PS-433540, Sitaxsentan sodium, Sodium Ferulate, TBC-11241 (Sitaxsentan), TBC-3214 (N-(2-acetyl-4,6-dimethylphenyl)-3-[[(4-chloro-3-methyl-5-isoxazolyl)amino]sulfonyl]-2-thiophenecarboxamide), TBC-3711, Trapidil, Treprostinil diethanolamine and Treprostinil sodium;

(xxi) ENACs:—Amiloride, Benzamil, Triamterene, 552-02, PSA14984, PSA25569, PSA23682 and AER002.

The inhaler may contain a combination of two or more active ingredients, for example a combination of two or more of the specific active ingredients listed in (i) to (xxi) herein above.

In one embodiment the inhaler contains an active ingredient selected from mometasone, ipratropium bromide, tiotropium and salts thereof, salemeterol, fluticasone propionate, beclomethasone dipropionate, reproterol, clenbuterol, rofleponide and salts, nedacromil, sodium cromoglycate, flunisolide, budesonide, formoterol fumarate dihydrate, terbutaline, terbutaline sulphate; salbutamol base and sulphate, fenoterol, 3-[2-(4-Hydroxy-2-oxo-3H-1,3-benzothiazol-7-yl)ethylamino]-N-[2-[2-(4-methylphenyl)ethoxy] ethyl]propane-sulphonamide hydrochloride, indacaterol, aclidinium bromide, N-[2-(Diethylamino)ethyl]-N-(2-{([2-(4-hydroxy-2-oxo-2,3-dihydro-1,3-benzothiazol-7-yl)ethyl] amino}ethyl)-3-[2-(1-naphthyl)ethoxy]propanamide or a pharmaceutically acceptable salt, thereof (e.g. dihydrobromide); N-Cyclohexyl-N$^3$-[2-(3-fluorophenyphenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate); a [2-(4-Chloro-benzyloxy)-ethyl]-[2-((R)-eyclohexyl-hydroxy-phenyl-methyl)-oxazol-5-ylmethyl]-dimethyl-ammonium salt (e.g. hemi-naphthalene-1,5-disulfonate); a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate); or a combination of any two or more thereof.

Specific combinations of active ingredients which may be incorporated in the inhaler include:—

(a) formoterol (e.g. as fumarate) and budesonide;
(b) formoterol (e.g. as fumarate) and fluticasone;
(c) N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide or a pharmaceutically acceptable salt thereof (e.g. dihydrobromide) and a [2-(4-Chloro-benzyloxy)-ethyl]-[2-((R)-cyclohexyl-hydroxy-phenyl-methyl)-okazol-5-ylmethyl]-dimethyl-ammonium salt (e.g. hemi-naphthalene-1,5-disulfonate);
(d) N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide or a pharmaceutically acceptable salt thereof (e.g. dihydrobromide) and a (R)-1-[2-(4-Fluoro-phenyl)-ethyl]-3-((S)-2-phenyl-2-piperidin-1-yl-propionyloxy)-1-azonia-bicyclo[2:2.2]octane salt (e.g. bromide or toluenesulfonate);
(e) N-Cyclohexyl-N$^3$-[2-(3-fluorophenyl)ethyl]-N-(2-{ [2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate);

N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl] amino}ethyl)-β-alaninamide or a pharmaceutically acceptable salt thereof (e.g. di-D-mandelate) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate).

BRIEF DESCRIPTION OF THE DRAWINGS

Preferred aspects and embodiments of the present invention will now be described, by way of example only, with reference to the accompanying drawings, in which:

FIG. 11 is a perspective side view of a lever of a releasable locking arrangement of an inhaler in accordance with the present invention;

FIG. 12 is a perspective front side view of the lever of FIG. 11 and a lever lock of the releasable locking arrangement;

FIG. 13 is a perspective front side view of the lever of FIG. 11 in its operating position in the chassis of FIG. 9;

FIGS. 21(a)-21(d) shows in perspective the wheels of a dose counting mechanism in accordance with the present invention;

FIGS. 22(a)-22(b) shows the wheels of FIGS. 21(a)-21(d) located in a counter chassis and having a translating member enclosing them therein, in accordance with the present invention;

DETAILED DESCRIPTION OF PREFERRED EMBODIMENTS

Figure 1:
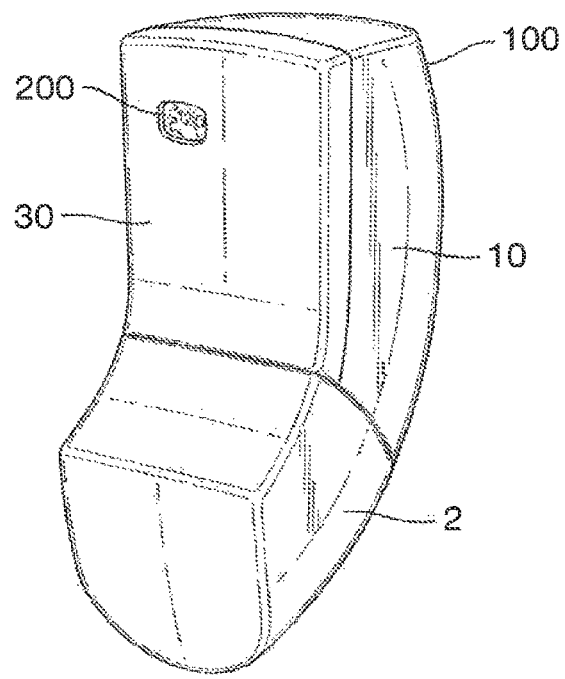
FIG. 1 is a front side perspective view of an inhaler in accordance with the present invention with the cap closed.

Referring now to FIG. 1, a breath actuated inhaler (BAI) 100, in accordance with embodiments of the present invention, is shown. The inhaler 100 comprises a housing or back cover 10, a mouthpiece cover or cap 2 and a front fascia 30 (shown in detail in FIG. 25) having an aperture 32 through which is visible a counter 201 of a counting mechanism 200. A magnifying protective cover (not shown) fills the aperture 32 and shields the counting mechanism 200 from ingress of dirt and other undesirable particulates, whilst enhancing the visibility and brightness of the counter digits. The fascia 30 preferably has a line of weakness (not shown) such that, if it is attempted to forcibly remove the fascia 30 and access the internal components, the line of weakness shows as a deformation or change in the plastic (e.g. colour change or other visible weakness) in the outer surface of the fascia 30, indicating that the inhaler 100 has been tampered with and should not be used.

Figure 2:
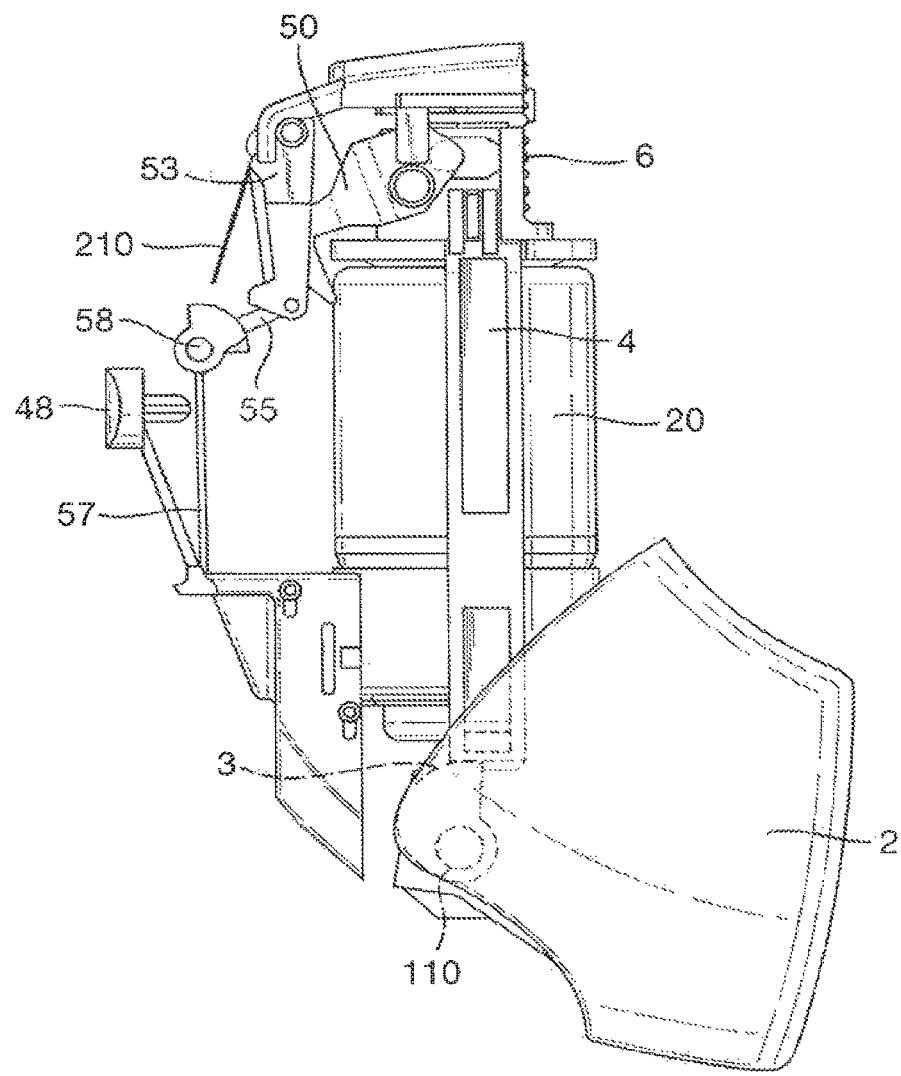
FIG. 2 is a schematic side view of some internal components of an inhaler in accordance with the present invention with the cap closed.
Figure 6:
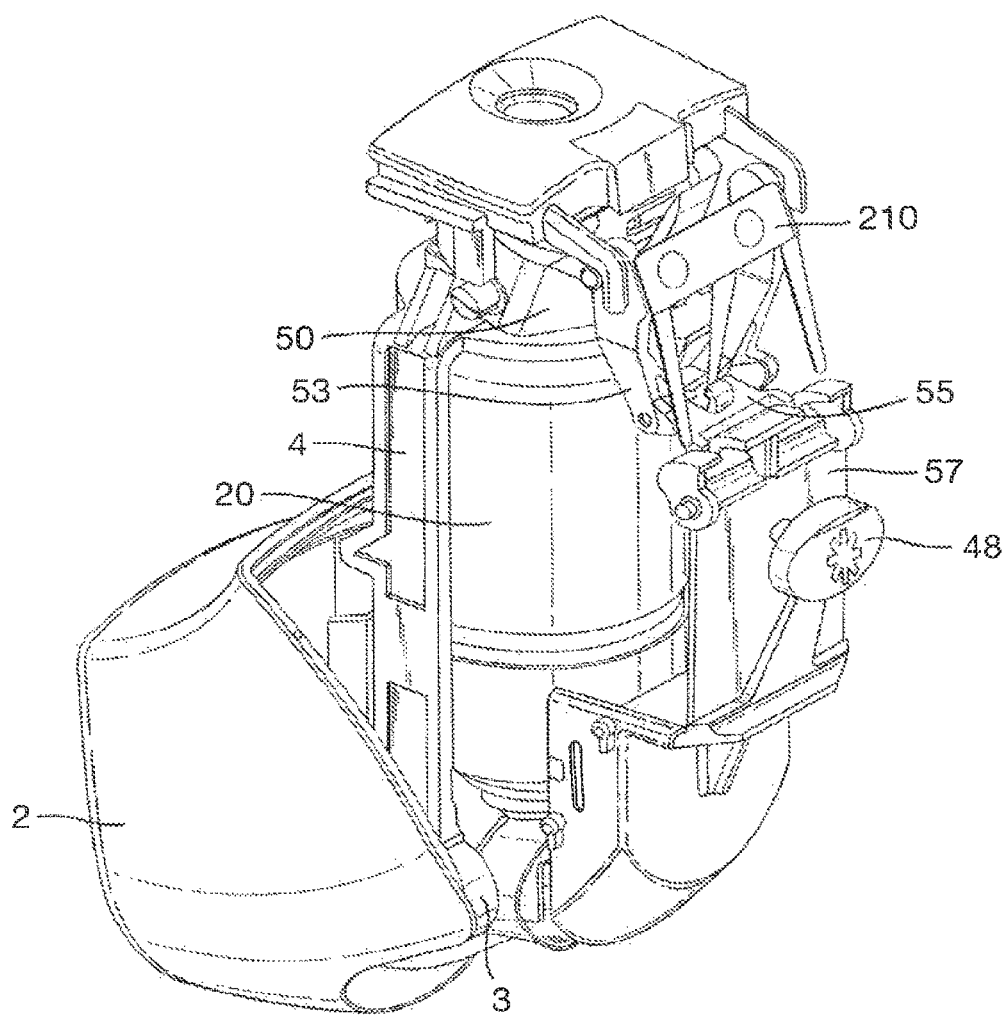
FIG. 6 is a schematic side view of the inhaler of FIG. 2.

FIG. 2 shows some of the internal components of the inhaler 100, as the back cover 10 and front fascia 30 has been removed. FIG. 6 also illustrates the components of FIG. 2 but in perspective view. In these figures, the inhaler 100 is in the neutral or rest position with the cap 2 closed and covering the mouthpiece 60, which is the preferred state of the inhaler 100 when it is not in use. A canister of medicament 20 (which typically holds a suspension or solution of one or more active pharmaceutical ingredients in a propellant under pressure) is housed in the inhaler 100. Such canisters 20 are well known in the art.

A yoke 4 is shown in its uppermost position and a coiled spring 6 is shown in a loaded state, thus storing an actuation or dispensing force. Most of the mechanical components of the inhaler, except the yoke 4, are unloaded and there is no compression of the canister 20. The yoke 4 is supported by the cap 2, specifically by a cam surface 3 of a cam 110 of the cap 2. Thus in the neutral position, the loaded spring force (typically of about 50 N) is held by the yoke 4, which is typically formed of a material that is resistant to flexing and buckling (such as polyoxymethylene, e.g. Ultraform® N 2720 (M60)). A lever 50 and a lever lock 53, both parts of a releasable locking arrangement, are each in their locked positions, although may not be under tension. A further component of the releasable locking arrangement is a drop link 55, which is shown in its latched position whereby it rests upon a pivot shaft 58 of a breath-actuated element, vane 57, thus able to hold the lever lock 53 in its locked position. A return spring 210 abuts the inner surface of the back cover 10 when the inhaler 100 is assembled, to bias the releasable locking arrangement into the locked position so that it will lock when under tension or load.

A manual firing button 48 is provided and enables the user to deliver a dose of medicament us un emergency function if, for any reason, the usual dispensing mechanism foils, or if the user otherwise cannot breath actuate the dispensing mechanism to deliver a dose of medicament, for example, during a chronic asthma attack. Alternatively the button 48 can be used to test and/or prime the inhaler 100, or simply as an alternative firing mechanism if desired.

Most of the mechanical components of the inhaler 100 are retained in a chassis 40, which is not shown in FIG. 2 but is shown in later figures (such as FIG. 9). Most of the components of the dispensing mechanism are pivoted on, engaged with, or supported by the chassis 40.

Figure 3:
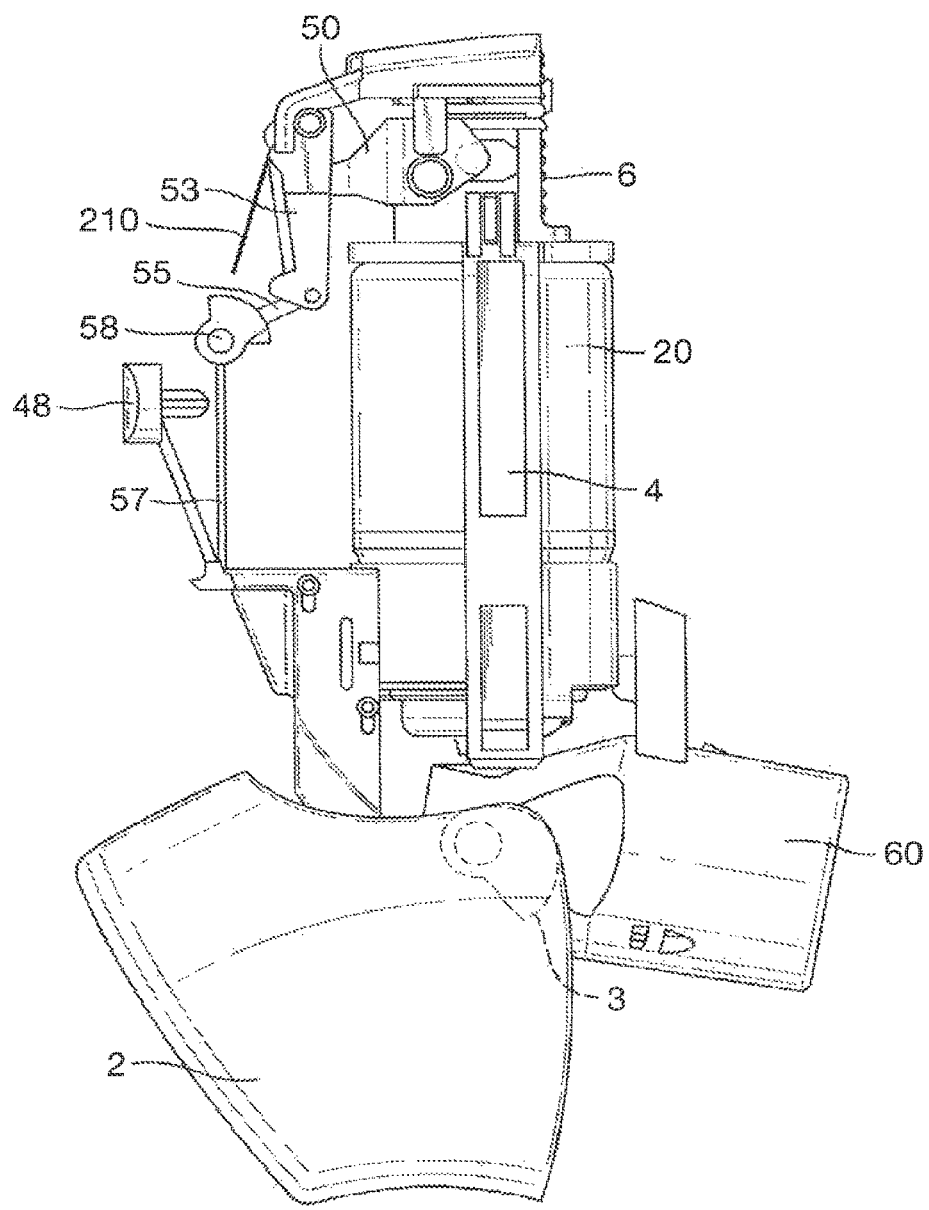
FIG. 3 is a schematic side view of the inhaler components of FIG. 2 with the cap open and the dispensing mechanism loaded and ready to dispense a dose.
Figure 7:
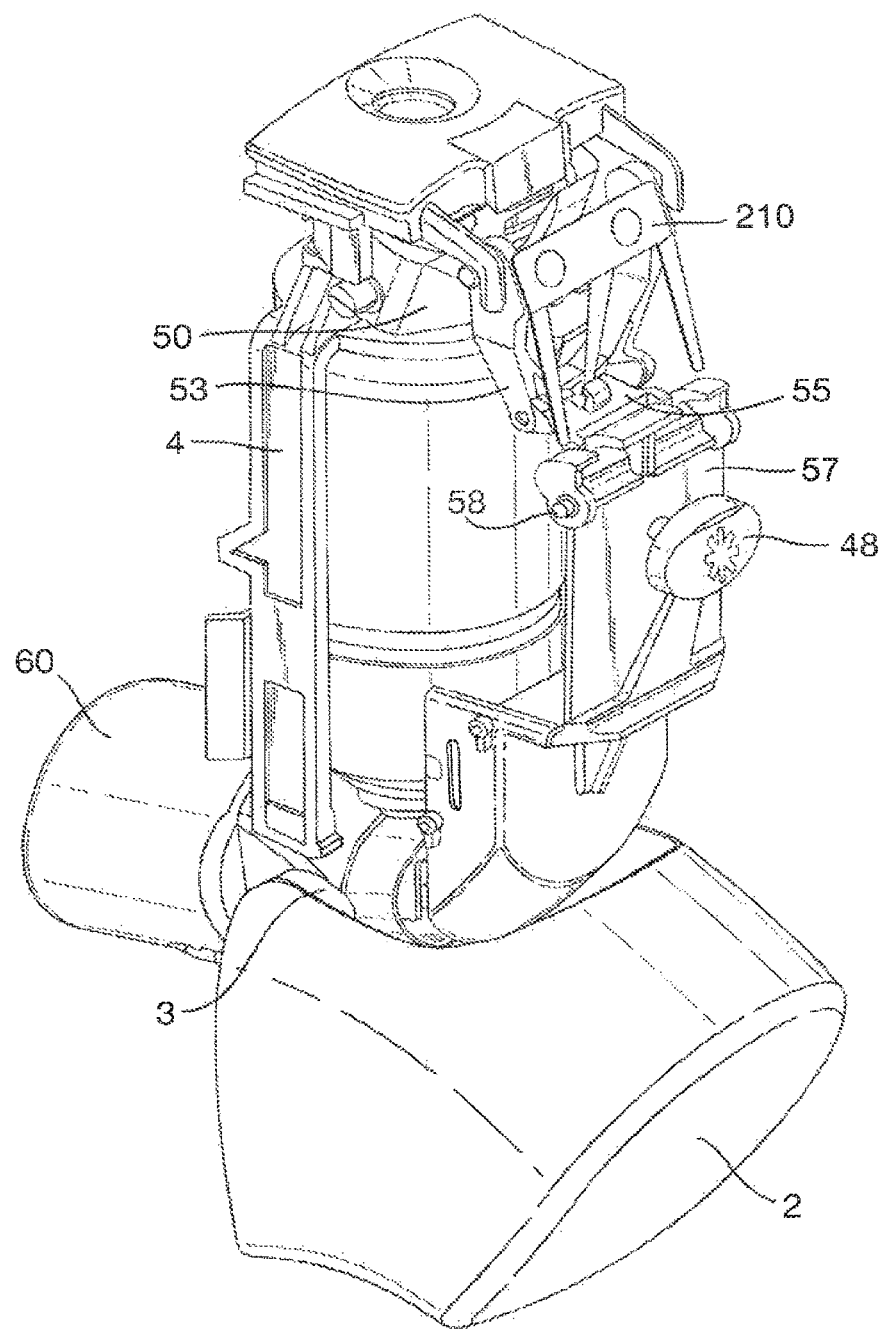
FIG. 7 is a schematic side view of the inhaler of FIG. 3.

FIG. 3 illustrates the inhaler 100 when it is ready to be used/fired. FIG. 7 also illustrates the components of FIG. 3 but in perspective view. The cup 2 is opened to uncover a mouthpiece 60. As the cap 2 pivots on opening, the yoke 4 moves downwardly under the force of the spring 6 to engage the base of the canister 20. However compression of the canister 20 to deliver a dose of medicament is substantially prevented by the releasable locking arrangement which becomes engaged as the yoke moves and holds the load of the spring 6, the lever lock 53 holding the lever 50. In this primed or dispensing state, the inhaler 100 is loaded, ready to fire and deliver a dose of medicament.

Inhalation by the user at the mouthpiece 60 causes air to flow through the air flow path defined inside inhaler 100. Due to the pressure drop created by the air flow (or use of the firing button 48 if manual actuation occurs), the vane 57 pivots and releases the drop link 55. The vane 57 is configured to be of a suitable size and shape such that it is able to move under a relatively low pressure drop, and the inhalation channel is configured to be curved at least where it corresponds with the a bottom edge of the vane 57, such that the gap between the edge of the vane 57 and the channel remains substantially the same as the vane 57 rotates under inhalation. Movement of the drop link 55 allows the lever lock 53 to release the lever 50, which is biased into its released position by the load of the spring 6 acting on the yoke 4 which pushes on the yoke protrusions 82 of the lever 50. The lever 50 in its unlocked state allows the coiled spring 6 to unload and to compress the canister 20 to deliver a dose of medicament. The dispensing mechanism also triggers an adjustment of the counter 201 of the counting mechanism 200 via a translating member 250 as discussed below and shown in FIG. 24.

Figure 4:
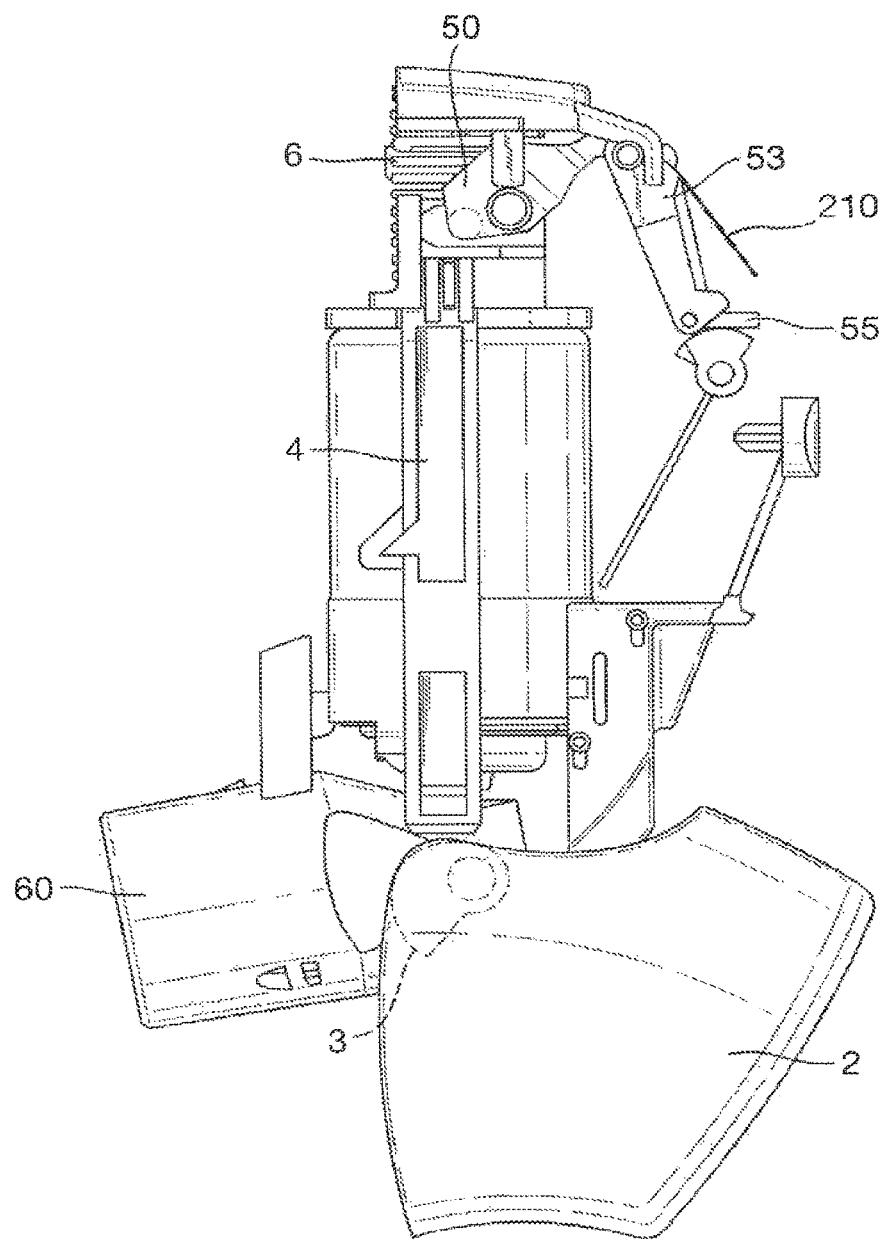
FIG. 4 is a schematic side view of the inhaler components of FIG. 2 with the cap open and the dispensing mechanism unloaded having dispensed a dose.
Figure 8:
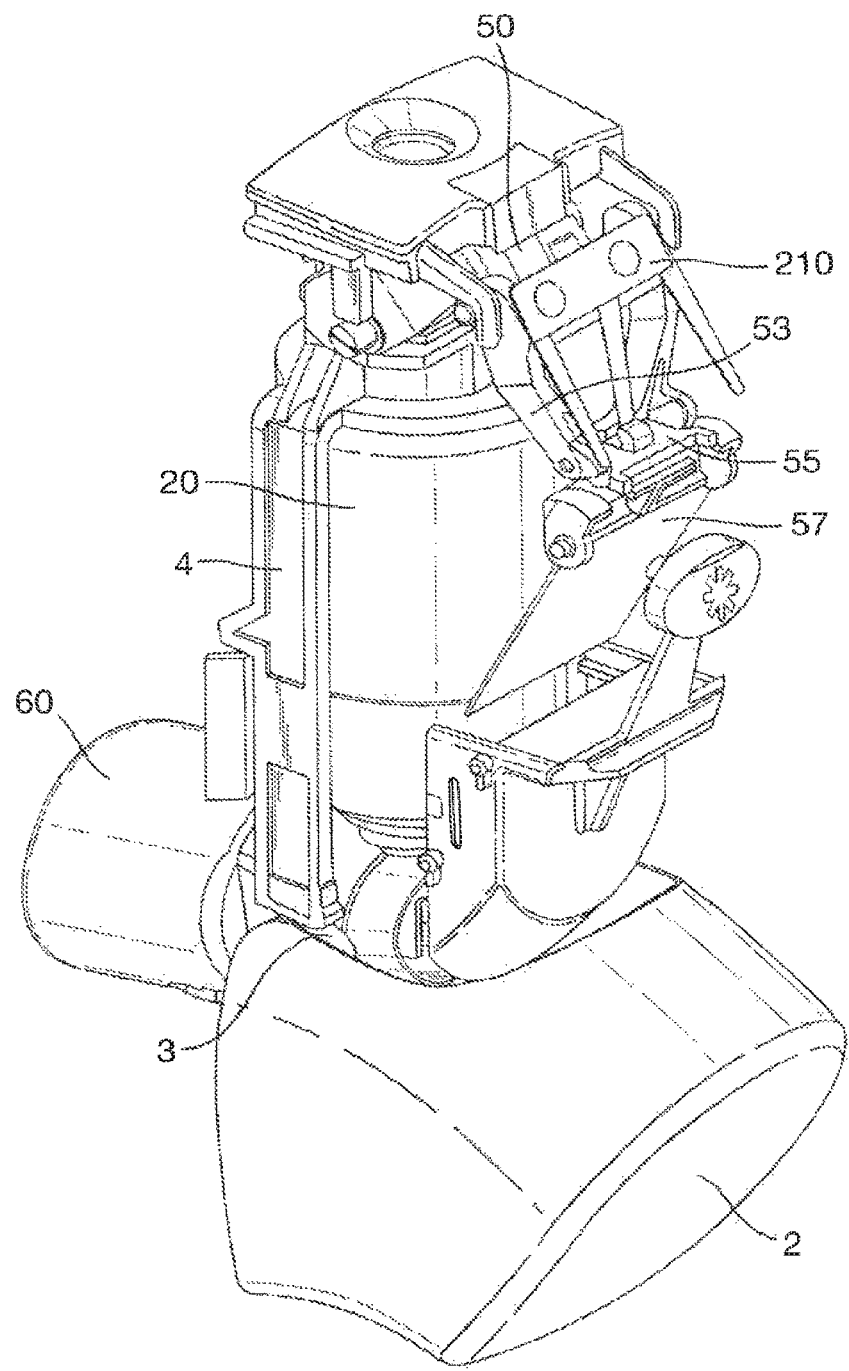
FIG. 8 is a schematic side view of the inhaler of FIG. 4.

FIG. 4 illustrates the components of the inhaler 100 after a dose of medicament has been dispensed. FIG. 8 also illustrates the components of FIG. 4 but in perspective view. In order to be able to dispense a further dose of medicament, the inhaler 100 must be fully reset from the FIG. 4 configuration to the dispensing state shown in FIG. 3. Fully resetting the inhaler 100 allows the metering valve 21 (see FIG. 5) of the canister 20 to refill with medicament. It also causes the lever 50 to return to a position where it can be locked by the lever lock 53, which is pushed back into its locking position by the spring 210. The drop link 55 is also pushed back into place by the spring, thus readying the releasable locking arrangement to again lock the dispensing mechanism and prevent actuation until the inhaler is fired.

Resetting of the inhaler 100 is achieved by closing the cap 2 so that the cam surface 3 pushes the yoke 4 upwards, which in turn pivots the lever 50, etc., and returns the inhaler 100 to the state shown in FIG. 3. Further details of the resetting mechanism are discussed below, in particular in relation to the prevention mechanism to prevent the inhaler 100 being only partially reset.

Figure 5:
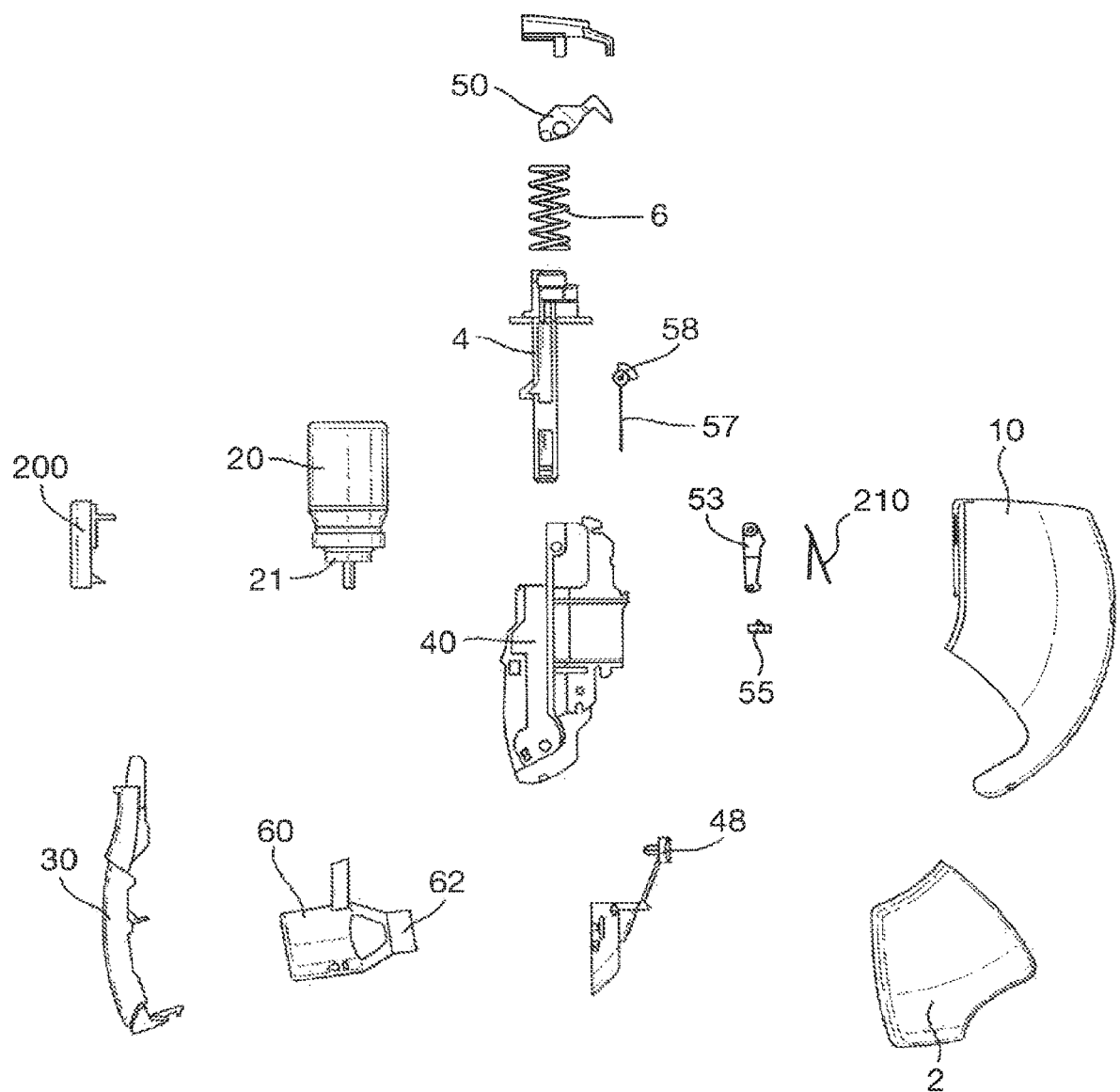
FIG. 5 is an exploded schematic view of the components of the inhaler of FIG. 1, which has the components shown in FIGS. 2 to 4.

FIG. 5 is an exploded view of a typical inhaler 100, such as one in accordance with embodiments of the present invention. The component parts are shown in the unassembled state. The counting mechanism 200 is shown separately but is insertable into the chassis 40 such that at least the display of the counter 201 of the counting mechanism 200 is visible through an aperture 32 in the fascia 30. A magnifying window formed integrally with the chassis of the counting mechanism 200 aligns with the aperture 32 as discussed in more detail below.

Figure 9:
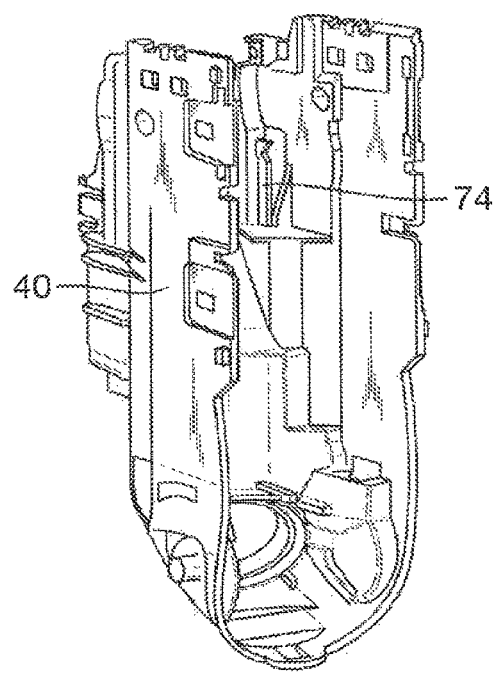
FIG. 9 is a perspective front side view of a chassis of an inhaler in accordance with the present invention.
Figure 10:
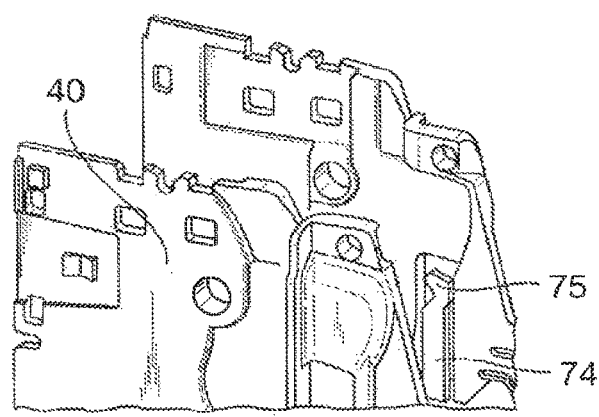
FIG. 10 is a close up view of the top portion of the chassis of FIG. 9, showing a component of the prevention mechanism.

FIGS. 9 and 10 show a chassis 40 in accordance with embodiments of the present invention. The chassis 40 comprises an injection moulded polyoxymethylene copolymer, such as Hostaform MT12U03, although other suitable materials and/or manufacturing techniques can be used to form a chassis 40 suitable for use in embodiments of the present invention. The chassis 40 is a primary structural component of the exemplified inhalers 100 and defines many of the pivot points of the inhaler mechanisms and also defines the position of many the other components of the inhaler 100.

Figure 20:
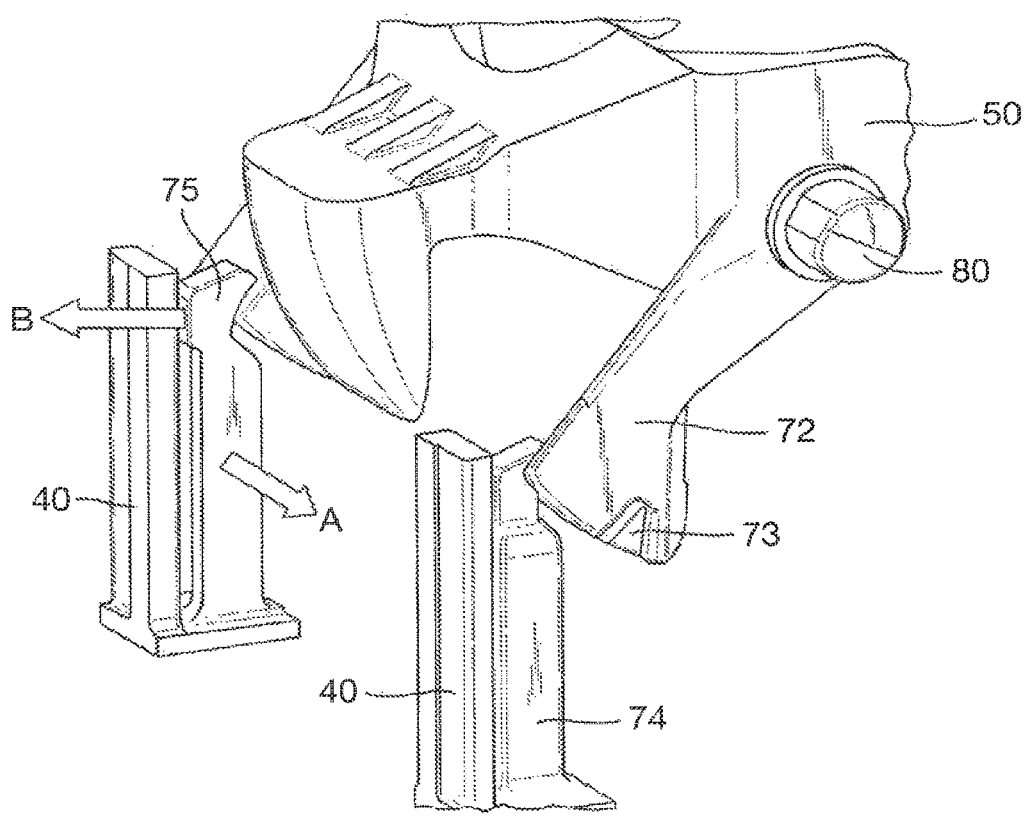
FIG. 20 is a perspective view of a prevention mechanism in accordance with the present invention.

In the embodiment shown in FIGS. 9 and 10, the chassis 40 also defines one of the components of a prevention mechanism 70. As mast clearly shown in FIG. 10, the chassis comprises an integrally formed second engaging member 74. The second engaging member 74 projects generally upwards when the chassis 40 is located in the inhaler 100 and the inhaler 100 is held in an upright position. The second engaging member 74 is sufficiently flexible such that it can be deflected out of the plane of the chassis side (i.e. in direction A as shown in FIG. 20 and also in a direction substantially directly opposite to A). At the upper end of the second engaging member 74 there is provided an engaging portion 75, which is a hooked-shaped portion having a protruding tooth or hammer head. The tooth is configured for engagement in a mating configuration with an engaging portion 73 of a first engaging member 72 which is shown in FIGS. 11 to 13. The tooth 75 is angled to aid in locating and retaining the tooth 75 in the engaging portion 73 of the first engaging member 72. The second engaging member 74 is also sufficiently flexible such that it can be deflected generally towards the chassis (i.e. in direction B as shown in FIG. 20) such that the tooth 75 is brought into abutment with the chassis 40. As well as being sufficiently flexible to be deflectable in this ways described above, the second engaging member 74 is also sufficiently resilient such that it will reliably return to its initial position once the deflecting force(s) is removed. Although only one second engaging member 74 is visible on the chassis 40 of FIGS. 9 and 10, there is provided a further second engaging member 74 of the same configuration but on the opposite side of the chassis 40, which is not visible in these figures.

FIG. 11 shows a lever 50 for the inhalers 100 shown in the figures. The lever 50 is a generally symmetrical component that is held in a pivotable configuration by the chassis 40. Chassis protrusions 80 (only one of which is shown in FIG. 11) are provided for engagement with the chassis 40 when the inhaler 100 is assembled (as shown in FIG. 13). In use, e.g., when dispensing a dose of medicament, the lever 50 pivots about these chassis protrusions 80. The lever 50 also comprises two yoke protrusions 82 (only one of which is shown in FIG. 11) which engage with the yoke 4 when the inhaler 100 is assembled such that movement of the yoke 4 (e.g. under the force of the spring 6 or when resetting the inhaler 100 using the cup 2) is translated to the lever 50 and pivots the lever 50 about the chassis protrusions 80.

Lever 50 further comprises a pair of counter protrusions 92 for engaging and actuating the counting mechanism 200 via a translating member 250 as discussed below. The counter protrusions 92 are curved such that, if the lever 50 rotates too far, die counter protrusions can disengage from the translating member 250 of the counting mechanism 200 to avoid overcounting or damage that may be caused to the translating member 250 by over rotation of the lever 50. Lever 50 also comprises an abutting protrusion 52 that is configured to rest against a portion of a lever lock 53 when die inhaler 100 is in its rest state (as shown in FIGS. 2, 6 and 12).

Lever 50 further comprises u pair of first engaging members 72 that protrude from the lever 50, each having a respective engaging portion 73 (only one shown in FIG. 11) generally at an end thereof. The engaging portions 73 are shaped to receive a tooth of the respective engaging portions 75 of the second engaging members 74 of the chassis 40. When the engaging portions 75 of the second engaging members are received in the engaging portions 73 of the first engaging members 72 any tensile force pulls the engaging members 72, 74 further into a mating configuration and prevents the engaging members 72, 74 being pulled apart. This arrangement locks the lever 50 against rotation about the chassis protrusions 80 even if the yoke 4 acts on the lever 50 via the yoke protrusions 82 and attempts to move it.

Figure 14:
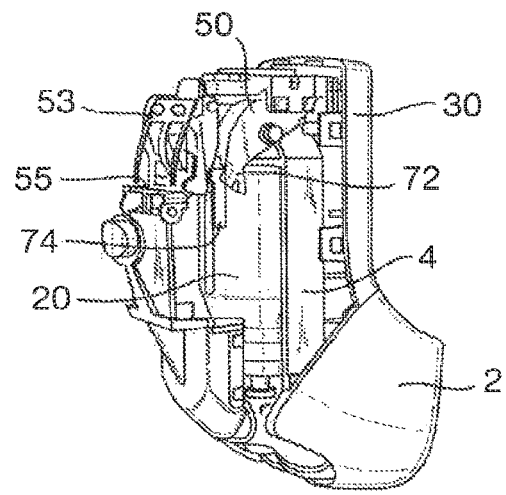
FIG. 14 is a perspective rear side view of the inhaler of FIG. 1 with the back housing or cover and certain other components removed to show the internal components and the cap in the closed position.

Operation of the inhaler 100 will now be described with a focus on the role of the prevention mechanism 70. FIGS. 14 to 17 show the inhaler 100 at different stages of operation. In FIG. 14, the inhaler 100 is in the neutral or rest state, which is the preferred state for storing the inhaler 100 between uses. The prevention mechanism 70 comprises a pair of first engaging members 72 integrally formed with the lever 50 (of which only one is shown in FIG. 14) and a pair of first engaging members 74 integrally formed with the chassis 40 (of which only one is shown in FIG. 14 and for clarity, the rest of the chassis 40 has been removed, including the portions against which the engaging portions 75 of the second engaging members 74 abut when the engaging portions are engaged in the mating configuration and are under load). In the rest state, the engaging portion 75 of the second engaging member 74 sits above and separate from the engaging portion 73 of the first engaging member 72. Furthermore the engaging portion 75 is not in contact with the substantially rigid component of the inhaler 100, which in the shown inhaler is another part of the chassis 40.

Figure 15:
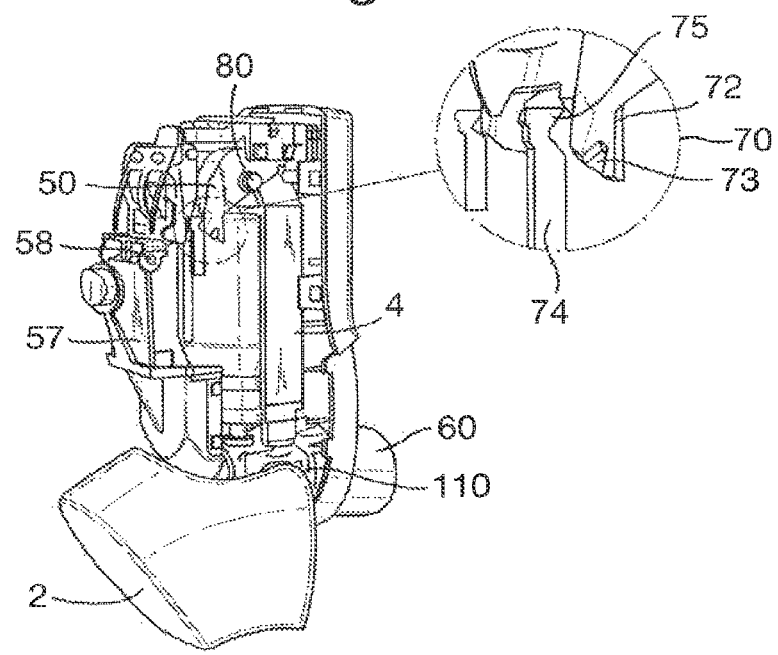
FIG. 15 is a perspective rear side view of the inhaler of FIG. 1 with the cap in the open position and the dispensing mechanism loaded and ready to dispense a dose.

When a patient wishes to inhale a dose of medicament, the first operation step is to open the mouthpiece cap 2 to expose the mouthpiece 60, as shown in FIG. 15. The cap 2 is pivotally mounted on the chassis 40 and has a cam 110 at the pivot point. Pivotal movement of the cap 2 from the second or closed position to the first or open position allows the yoke 4 to move downwards, under the force applied by the coiled spring 6. As the yoke 4 moves downwards the load of the compressed spring 6 transfers from the yoke 4 (which rests on the cam surface 3, when the cap 2 is fully closed), to being held by the releasable locking arrangement, as the cap 2 is opened. Specifically as the cap 2 opens, the lever 50 rotates and the lever abutting protrusion 52 contacts with, and is locked by, the lever lock 53 which is held by the drop link 55 that rests on the pivot shaft 58 of the vane 57 to hold the load of the spring 6. This can be seen in FIG. 15, as when the cap 2 is fully opened, there is space between the foot of the yoke 4 and the cam surface 3 of the cap 2. Although, us the load is transferred to the releasable locking arrangement the lever 50 pivots slightly about the chassis protrusions 80 as the yoke 4 moves downwards, any such movement of the lever 50 will be minimal and will not engage or otherwise affect the prevention mechanism 70, as can be seen in the close-up view of FIG. 15.

After opening the cap 2 of the inhaler 100, thus priming it such that a dose is ready to be dispensed (known as the prefire point or condition), the patient inhales through the mouthpiece 60. The pressure drop in the airflow passage through the inhaler 100 releases the releasable locking mechanism. Specifically the pressure drop causes the vane 57 to pivot about its axis 58 generally towards the mouthpiece 60, which allows the drop link 55 to disengage from the top surface of the vane, thus allowing the lever lock 53 to be pushed away by the lever abutting protrusion 52, which frees the lever 50 to pivot on the chassis protrusions 80 under the force of the expanding spring 6 (which acts on the yoke 4 which in turn acts on the lever 50 via the yoke protrusions 82). The downward movement of the yoke 4 under the full force of the compressed spring 6 compresses the valve stem 24 of the canister 20 against u nozzle block 62 of the inhaler 100 (in this embodiment, the nozzle block 62 is an integral part of the mouthpiece 60 but it could be a separately provided component or formed with another component of the inhaler 100). Compression of the valve stem 24 activates the metering valve and dispenses a dose of medicament under pressure into the inhalation airflow and through the mouthpiece 60 lobe inhaled by the patient.

Figure 16:
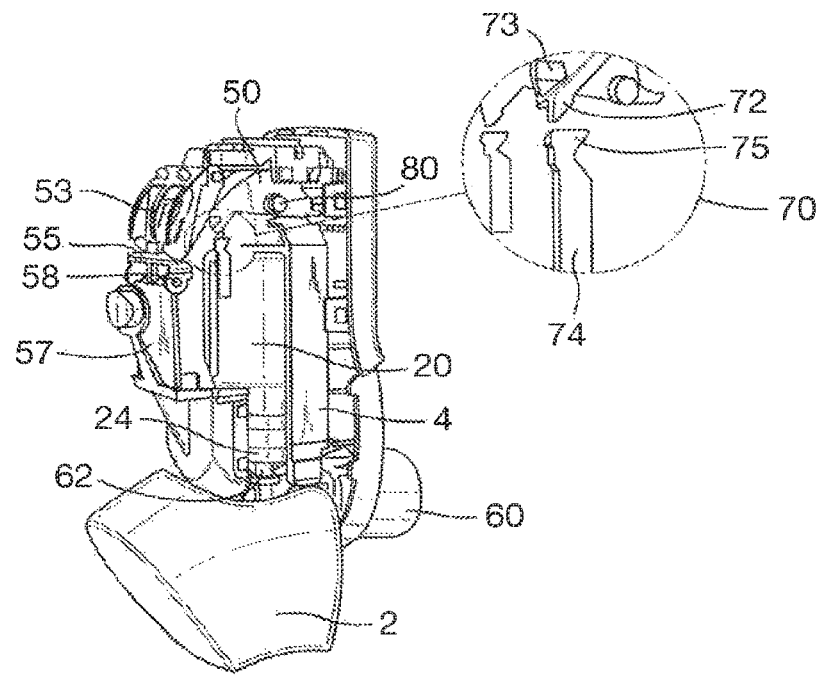
FIG. 16 is a perspective rear side view of the inhaler of FIG. 1 with the cap in the open position and the dispensing mechanism unloaded having dispensed a dose.

FIG. 16 shows the inhaler 100 after this sequence has occurred, i.e. in the fired or dispensed state, where a dose of medicament has been dispensed and the inhaler 100 has not been reset. The yoke 4 has been deployed under the load of the spring 6 and has moved downward back toward contact with the cam surface 3 of the cap. The lever 50 has pivoted relative to the chassis 40 such that the counter engaging portion 92 has moved downwards and actuated the counting mechanism 200 and the first engaging member 72 has moved upwards. In FIG. 16, the vane 57 has returned to its rest position because the patient has stopped inhaling. However the other components of the releasable locking arrangement cannot return to the rest or neutral position as the abutting protrusion 52 of the lever 50 is still pushing upwards on the lever lock 53 due to the position of the lever 50.

As mentioned above, as the lever 50 pivoted about the chassis protrusions 80, the end of the lever 50 having the first engaging member 72 (or members as can be seen in the FIG. 16 close up) moved upwards. As can be seen in FIG. 16, in the dispensed state, the engaging portion 73 of the first engaging member 72 has travelled such a distance that it has travelled past the engaging portion 75 of the second engaging member 74 and has finished above and spaced away therefrom. Clearly it is undesirable for the engaging portions 73, 75 of the engaging members 72, 74 to engage in a mating configuration during dispensing of a dose of medicament. Therefore the engaging portions 73, 75 are configured such that if the first engaging member portion 73 moves upwards from a position below the second engaging member portion 75, then as the engaging portions 73, 75 come into contact, one or both of the engaging portions 73, 75 is deflected by the other of the engaging portions 73, 75 such that they pass each other without engaging in the mating configuration. In the present embodiment, the engaging portions 75 of the second engaging members 74 (i.e. those formed on the chassis 40) are deflected inwardly (i.e. are squeezed slightly towards each other) by the more rigid engaging portions 73 of the first engaging members 72 (i.e. those formed, on the lever 50).

After inhaling a dose of medicament, the patient is encouraged to reset the inhaler 100 by the configuration of the device, since it is not possible to dispense further doses until it has been fully reset. This not only ensures that the inhaler 100 is returned to its preferred rest state (in which it is configured to hold the load of the spring 6 through the yoke 4, which is a relatively strong component of the inhaler 100 and is designed to hold such a load reliably and without damage thereto) but also that the mouthpiece 60 is covered straight after use, thus preventing or minimising ingress of dirt and other undesired to particles or contaminants into the inhaler 100. To reset the inhaler 100, the patient only needs to pivot the cap 2 back from the first (open) position to the second (closed) position. The cam 110 of the cap 2 is engaged with the yoke 4 and as the cap 2 rotates, the cam surface 3, which is helically shaped, helps push the yoke 4 upwards, thus reloading the spring 6 and moving the other components, particularly those of the releasable locking arrangement, back into the rest state.

However, it is possible that the patient might not fully reset the inhaler 100, i.e. may not move the cap 2 all the way from the first, open position to the second, closed position. This may be because, for example, the patient is distracted during the resetting motion and releases the cap 2, or the patient may lose their grip on the cap 2, or it may be that the patient plays with the cap land repeatedly move it partially in and out of the open position, without ever fully closing the cap 2. This is undesirable as it might lead to the inhaler 100 not fully functioning when the next dose is dispensed, for example because the metering valve does not fully refill, or insufficient load is stored in the spring 6 to fully activate the valve. Still further, the inhaler 100 may not be reset to the point at which the counting mechanism 200 is reset, which means that any dose dispensed subsequently, even if not a full dose, will not be counted and the counter 201 may therefore inaccurately reflect the number of doses of the inhaler 100.

Figure 17:
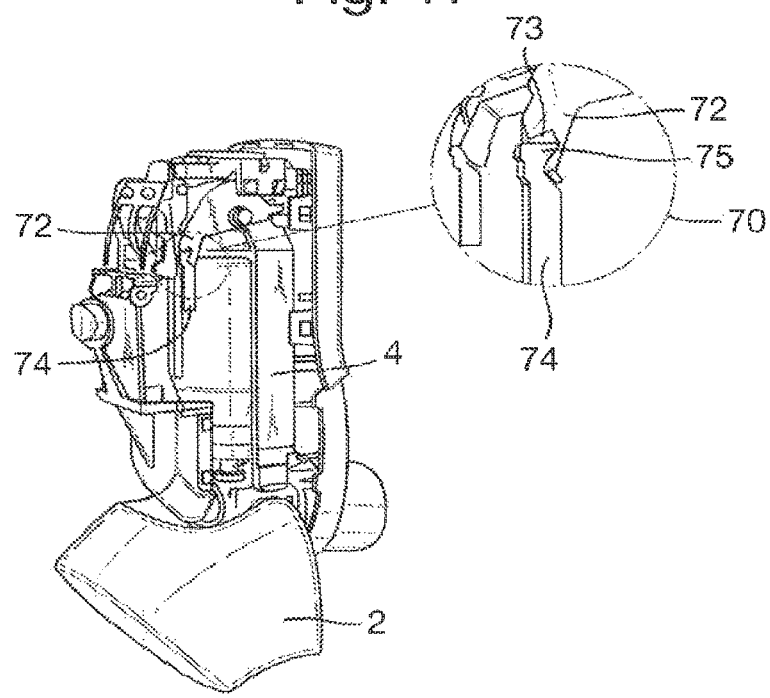
FIG. 17 is a perspective rear side view of the inhaler of FIG. 1 with the cap in the open position and the dispensing mechanism partially reset, with the reset load being held by the prevention mechanism.

The prevention mechanism 70 is configured to solve all the above problems. If the cap 2 is not fully moved from the open position to the closed position, i.e. if the patient stops rotating the cap 2 when it is in some intermediate position and the spring force would therefore bias the yoke 4 to rotate the cap 2 back into the open position, the prevention mechanism 70 engages to hold the load of the spring 5 until the cap 2 completes it movement to the fully closed position, in which the inhaler 100 is fully reset. Thus the yoke 4 is not biased by the spring 6 as the prevention mechanism prevents such biasing. As can be seen in FIG. 17, the engaging portions 73, 75 are configured such that if the second engaging member portion 75 moves upwards from a position below the first engaging member portion 73, then as the engaging portions 73, 75 come into contact they are capable of engaging in the mating configuration, should rotation of the cap 2 to the closing position cease. In the present embodiment, in order to optimise the mating engagement, engaging portions 73, 75 are configured such that as they initially come into contact, one or both of the engaging portions 73, 75 is deflected by the other of the engaging portions 73, 75 such that the deflected engaging portion(s) snap into the mating configuration. In the present embodiment, the engaging portions 75 of the second engaging members 74 (i.e. those formed on the chassis 40) are again deflected, but this time outwardly (i.e. are deflected slightly away from each other) by the more rigid engaging portions 73 of the first engaging members 72 (i.e. those formed on the lever 50). Once the engaging portions 75 have passed beyond a certain point, they deflect back inwards (as the material from which they are formed is relatively resilient) and snap or slot into the engaging portions 73 of the first engaging members 72, which are sized and shaped to snugly receive the teeth of the engaging portions 75 of the second engaging members 74. This configuration can be seen in FIG. 17. Once engaged in the mating configuration, should the cap 2 cease to move and/or move in the opposite direction (i.e. move back towards the first, open position) the load of the spring 5 is held (via the lever 50) by the first engaging members 72 which are pulled in their engaged state against the second engaging members 74. As the second engaging members 74 are flexible, the engaging portions 75 thereof are deflected under this tension generally in direction B (as shown in FIG. 20) and abut a more rigid part of the chassis 40. The tensile load placed on the engaging members 72, 74 in this manner does not disengage the mated engaging portions 73, 75, but rather they are driven together in the mating configuration and by virtue of the abutment with the chassis 40, the force of the spring 6 is readily withstood by a mixture of tension between the first and second engaging members 72, 74 and compression of the engaging portions 75 of the second engaging members 74 against the more rigid portion of the chassis 40. Thus the first and second engaging members 72, 74 are strong and reliable and will not suffer significant material creep nor permanent damage or deflection.

When the cap 2 resumes its motion towards the second, closed position however, the force through the second engaging members 74 is relieved and they return to their rest position (i.e. no longer abut the chassis 40) and the engaging members 72, 74 are effectively pushed together or compressed by the resumed movement of the lever 50. The engaging members 72, 74 are configured such that a compressive force or motion readily disengages the mated engaging portions 73, 75 (in this embodiment, by the more rigid engaging portions 73 of the lever 50 again deflecting the chassis engaging portions 75 outwardly). The cap 2 can then progress to the fully closed state and the inhaler 100 will be fully reset thus providing an inhaler 100 that will reliably dispense and count any further doses of medicament.

Although the above disclosed embodiments of the present invention have first and second engaging members 72, 74 integrally formed with the lever 50 and the chassis 40 respectively, this is an exemplary arrangement and is not limiting to the scope of the present invention. Alternative arrangements are envisaged, for example one or both of the engaging members 72, 74 may be separately formed components and/or one or both of the engaging members 72, 74 may be integrally formed with one or more other components of the inhaler 100. The more rigid component of the inhaler 100 against which the first and/or second engaging members 72, 74 abuts may be a component of the chassis 40 as discussed above, but may alternatively or additionally be any other suitable component.

Figure 18:
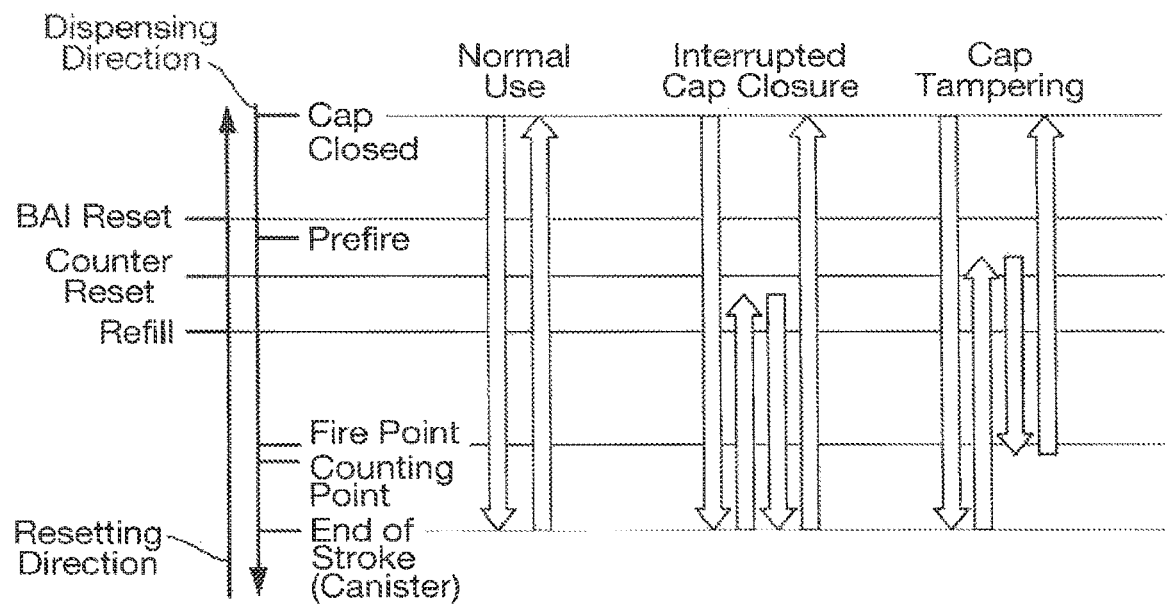
FIG. 18 schematically shows the various stages of operation and potential misuse of a typical breath actuated inhaler, FIG. 19 schematically shows the various stages of operation of a breath actuated inhaler having a prevention mechanism in accordance with the present invention.
Figure 19:
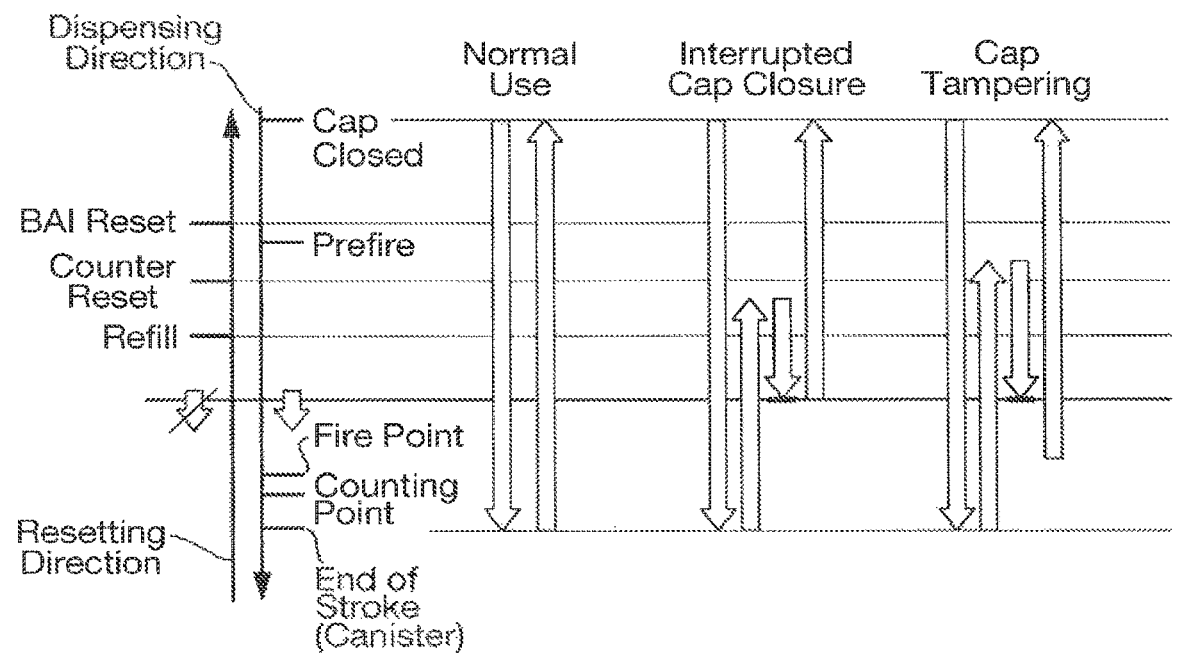

FIGS. 18 and 19 schematically illustrate the above operation of an inhaler 100 in accordance with the present invention, with reference to the various trigger points in the operating cycle. Under normal use, starting from the inhaler 100 rest or neutral position (cap closed), the cap 2 must be opened which, as shown under normal operation (closest to the left axis in both figures) moves the inhaler 100 in the dispensing direction through the following steps, in order: (i) the yoke 4 contacts the canister 20 (assuming it does not rest in a contracted state); (ii) the mechanism reaches the prefire point, where the inhaler 100 is primed and ready to fire (but is presented from doing so by the releasable locking arrangement. Thereafter, when the inhaler 100 is actuated/fired, the inhaler 100 operates in a dispensing direction through the second part of the cycle in which: (iii) the mechanism compresses the canister past the valve firing point (fire point), at which a dose of medicament is dispensed; (iv) the mechanism passes the counting point at which the counting mechanism 200 is actuated and a dose is counted by the counter 201; and finally (v) the mechanism reaches the end of stroke (final rest/dispensed) position. Steps (iii) and (iv) typically occur in the above order although step (iv) can occur before step (iii). In inhalers in which a dose is automatically counted as the inhaler fires, it is essential that every dose is counted and that the counter never counts when a dose is not dispensed. To achieve this, ideally the fire point and counting point should be as close together as possible to minimise the potential for one to be reached without then reaching the other (i.e. steps (iii) and (iv) occur as close together as possible, no matter in which order they occur). Furthermore, to ensure a full dose of medicament is always dispensed, such ab inhaler must be fully reset, at least past the prefire point and preferably past the BAI reset point before a subsequent dose is dispensed. Resetting occurs when the inhaler 100 moves in the resetting direction through the following steps, in order: (i) the mechanism passed the valve 21 reset point (i.e. the refill point, which is the position that, when the inhaler 100 is reset by rotation of the cap 2 in the resetting direction, the mechanism must reach for the valve 21 of the canister 20 to begin to refill; (ii) the mechanism passes the counter 201 reset point (i.e. the position that, when the inhaler 100 is reset by rotation of the cap 2 in the resting direction, the mechanism must reach to be ready to subsequently count another dispensed dose); (iii) the mechanism passes the inhaler 100 reset point (i.e. the BAI rest which is the position that, when the inhaler 100 is being reset by rotation of the cap 2 in the resetting direction, the mechanism must reach to be fully reset and ready to subsequently actuate/refire).

As shown in FIG. 18, if the device is not fully reset (i.e. does not reach the BAI reset due to, e.g., incomplete cap closure (such as interrupted cap closure or cap tampering)), it is still possible for the inhaler to dispense at least a partial further dose that may be counted as a whole dose. In the interrupted cap closure example, the cap 2 ceases movement when the inhaler 100 has passed the refill point, so the valve 21 begins to fill with medicament, but before the counter reset point is reached. Therefore if the inhaler 100 refires, whatever does has filled the valve 21 is released (at the fire point), but is not counted (although the inhaler 100 passes back through the count point, the counter has not been reset so no count occurs). Thus the inhaler 100 undercounts. In the cap tampering example, the inhaler 100 passes beyond the counter reset point, but does not reach the BAI reset. In the dispensing direction, cap 2 movement is reversed after the fire point but before the counting point (even though they are close together), so a dose is dispensed but not counted as the count point is not reached. Thus the inhaler 100 undercounts. The inhalers of FIG. 18 are not in accordance with the present invention as there is no mechanism to prevent actuation (or at least prevention of the inhaler 100 reaching the fire/count point) when the inhaler has not been fully reset.

FIG. 19, however, shows operation of an inhaler 100 in accordance with the present invention, having a prevention mechanism as previously described. As is shown in the figure, normal operation does not differ from the FIG. 18 examples. However, when cap 2 closure is interrupted or the cap 2 is tampered with before the inhaler 100 is reset to at least the BAI reset point, the prevention mechanism engages and prevents movement in the dispensing mechanism beyond a blocked point (shown as the horizontal red line). The blocked point is before the inhaler 100 can reach the fire or counting point. Thus the dispensing mechanism does not dispense nor eth counter count as the inhaler 100 cannot reach the fire point or counting point, until the cap 2 is closed and the inhaler 100 reset at least to the BAI reset point.

Figure 23:
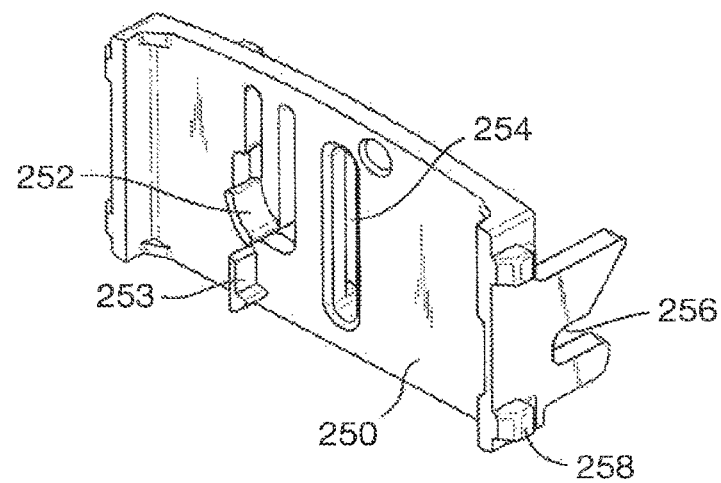
FIG. 23 is a perspective view of the translating member of FIG. 23.

FIGS. 21 to 23 show the main components of the dose counting mechanism 200. In FIG. 21, the first count wheel 220, the second count wheel 230 and the intermediate wheel 240 are shown. Both a front face 222 and a back surface 224 of the first count wheel 220 are shown in FIGS. 21(*c*) and 21(*d*) respectively. Front face 222 of the first count wheel 220 has numbers printed annularly thereon (not shown) from 0 to 9 which, when the first count wheel 220 is aligned on the first axis 260 of a counter chassis 202 (see FIG. 22) are concentric with, and aligned inside of, annularly printed number 1 to 12 (not shown) on a front face 232 of the second count wheel 230. The first (or units) count wheel 220 has annularly spaced teeth 226 arranged on the back surface 224, which are configured such that the notches therebetween receive a pawl 252 of the translating member 250. Movement of the translating member 250 in the counting direction C (FIG. 22) thus engages between the teeth 226 and rotates the unit count wheel 220 such that the number shown in the display window 280 of the dose counting mechanism 200 is decremented (for example from 9 to 8). However further rotation of the units count wheel 220 (e.g. such that digit 8 passes the window 280) is prevented by an overcount preventing protrusion 253 of the translating member 250. This overcount preventing protrusion 253 is a linear protrusion which protrudes from the face of the translating member 250 towards the back surface 224 of the units count wheel 220. The overcount preventing protrusion 253 is shaped and positioned on the translating member 250 such that it is capable of abutting one of a plurality of spaced apart ribs 228 arranged annularly around the outer part of the units count wheel 220 back surface 224. The overcount preventing protrusion 253 slides into a positon where it becomes located between a first (leading rib 228 and a second (following) rib 228 of the units count wheel 220 as the translating member 250 moves linearly in the counting direction C (at the same speed as the pawl 252 of the translating member 250). The ribs 228 and the overcount preventing protrusion 253 are configured such that the protrusion 253 abuts the second (following) rib 228 as the units count wheel 220 reaches the end of its desired increment. The overcount preventing protrusion 253 thus blocks the units count wheel 220 from rotating any further. As the translating member 250 returns to its initial position (i.e. moves linearly in a direction opposite the counting direction C), the overcount preventing protrusion 253 also moves linearly back to its initial position and is withdrawn from the abutment with the rib 228 of the units count wheel 220, thus freeing the wheel 220 to turn again on the next actuation.

The translating member 250 further comprises a rest count preventing protrusion (not shown) which also protrudes from the same face of the translating member 250 as the overcount preventing protrusion 253. The rest count preventing protrusion prevents rotation of the units count wheel 220 when the counting mechanism 200 is in the rest positon by engaging one of the plurality of ribs 228 of the units count wheel 220. Thus the rest count preventing protrusion and the overcount preventing protrusion 253 are somewhat complementary. The rest count preventing protrusion is also a linear protrusion and is similar in configuration to the overcount preventing protrusion 253.

The units count wheel 220 further comprises a pincer 221 which is configured to engage with the intermediate wheel 240 once per full rotation of the units count wheel 220 (i.e. after the units count wheel 220 has displayed digits 9 through to 0 in the display window 280). The pincer 221 rotates into position and engages with a long tooth 242 of the intermediate wheel 240. As the units count wheel 220 continues to rotate, the intermediate wheel 240 rotates as well, about axis 270 of the counter chassis 202 on which it is rotatably located. As the pincer 221 rotates still further, it disengages with the long tooth 242 of the intermediate wheel 240 and the intermediate wheel stope rotating until the pincer has rotated another full rotation and reengages therewith.

Rotation of the intermediate wheel 240 effects rotation of the second (or tens) count wheel 230, as the intermediate wheel 240 is engaged with the tens count wheel 230 via the interaction of tens count wheel teeth 234 and intermediate count wheel long teeth 242 and also short teeth 244. The interaction and relative positions of the wheels 220, 230 and 240 can be seen in FIG. 22. Thus tens count wheel 230 is selectively rotated one increment for every ten increments of the units count wheel 2220, via intermediate wheel 240, and the counter display counts down the digits from 120, which can be seen by a patient through the display window 280 which is located in the aperture 32 of the front fascia 30 (see FIG. 25). As the count of the display approaches and reaches zero, a flag 236, which protrudes inwardly from the tens count wheel 230, is brought into registration and occludes the display window 280. The flag is coloured red 236 and indicates to the patient that the inhaler has no doses of medicament remaining. Although the units wheel 220 may continue to rotate, the digits displayed thereon cannot be seen through the flag 236 and there is no confusion for the patient since it remains clear that no doses are remaining. To prevent the flag 236 rotating away from the display window 280, the tens count wheel 230 is configured such that a set of the teeth 234 are missing from the wheel 230 at a positon 233 that coincides with the flag 236 occluding the window 280. Therefore, even if the intermediate wheel 240 rotates, there are no teeth 234 of the tens count wheel 230 to engage with the teeth 242, 244 of the intermediate wheel 240 and the flag 236 will remain in the window 280.

FIG. 23 shows the translating member 250 of the dose counting mechanism 200. A slot 254 is provided for receiving a protrusion (not shown) from the first axis 260 on which the tens and units counts wheels 220, 230 are located. The slot 254 guides the translating member 250 as it moves in the counting direction C and back in the opposite direction and ensures reliable linear motion thereof. The linear movement of the translating member 250 is also aided by pairs of tabs 258 on either lateral edge thereof, which are received in channels 204 of the counter chassis 202. The tabs 258 hold the translating member 250 securely in place in the counter chassis 202 and abutting the relevant parts of the dose counting mechanism 200, whilst allowing the translating member 250 to move in the counting direction (and the opposite direction to reset the counter) by sliding in the channels 204.

Figure 24:
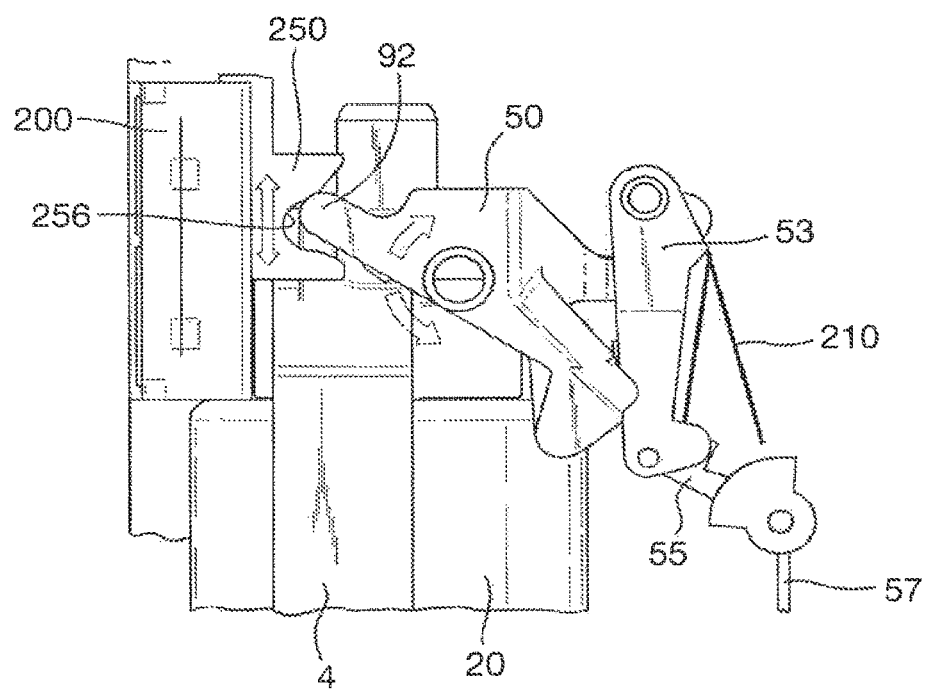
FIG. 24 schematically illustrates the interaction between a dispensing mechanism and a dose counting mechanism via a translating member, in accordance with the present invention.

The translating member 250 further comprises notches 256 for receiving a component of the inhaler dispensing mechanism, in this embodiment the protrusions 92 or the lever 50 as shown in FIG. 24. As the lever 50 rotates during dispensing of a dose of medicament, the protrusions 92 engage and push the translating member 250 downwards via notches 256, thus actuating the dose counting mechanism 200 and counting a dose. The protrusion 92 and notches 256 are suitably configured such that they will engage and disengage at appropriate points in the dispensing/counting cycle and will not force the dose counting mechanism 200 to overcount. In particular, the notches 256 and protrusion 92 are curved to enable disengagement if needed as the dose counting mechanism 200 is reset.

Figure 25:
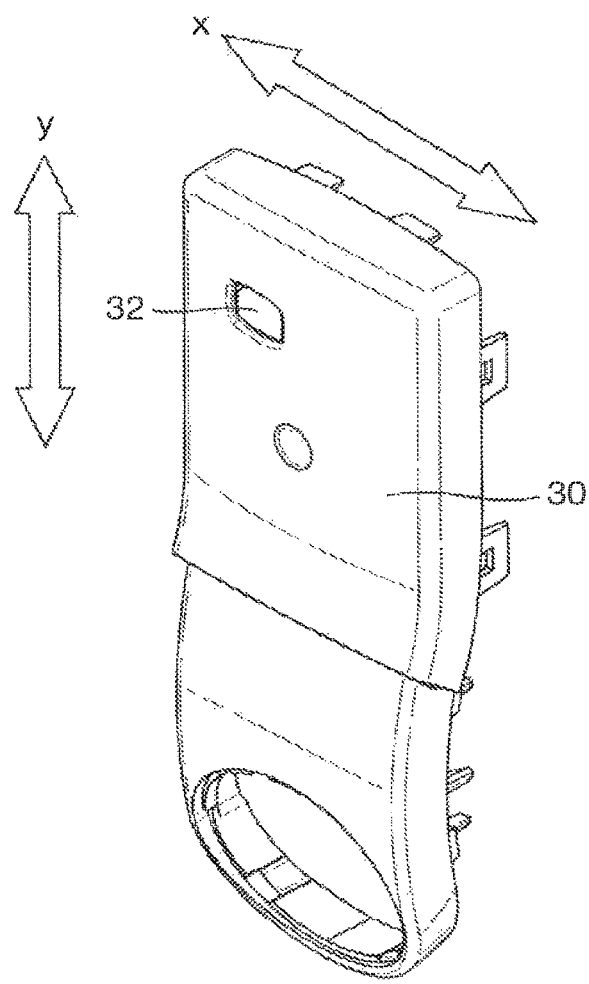
FIG. 25 is a perspective view of a front fascia for an inhaler in accordance with the present invention.

FIG. 25 shows a front fascia 30 of the inhaler 100 of the present embodiment. An aperture 32 is located where the fascia 30 covers the dose counting mechanism 200 so that the display window 280 is visible. Although not shown, the window 280 comprises a transparent plastic (amorphous copolymer like Eastman Tritan TX2001) component of the counter chassis 202 and is curved on its outer face in both the x direction and the y direction and protrudes from the counter chassis 202 into the aperture 32. The window 280 has a level of magnification that is greater in the y dimension (i.e. across the height of the window 280) than it is in the x direction (.e. across the width of the window 280). Thus although the display is magnified by the window 280, the display is not significantly distorted, particularly in the width dimension which is advantageous for reading digits. The window 280 of the present embodiment has a magnification in the x direction that magnifies the size of the display by about 10% and a magnification in the y direction that magnifies the size of the display by about 20%.

The invention claimed is:

1. An inhaler for delivery of a medicament by inhalation, the inhaler comprising:
    a dose counting mechanism having a counter and a translating member, the translating member including a pawl and the counter including a first count wheel, which comprises a plurality of annularly spaced ribs protruding from an outer face thereof, a second count wheel and an intermediate wheel engaged with the second count wheel and in selective engagement with the first count wheel,
    a dispensing mechanism configured, when actuated, to dispense a dose of medicament, wherein:
    upon actuation, the dispensing mechanism moves the translating member in a linear direction, whereby the pawl rotates the first count wheel, and
    as the first count wheel rotates, the intermediate wheel is selectively engaged thereby selectively rotating the second count wheel
    wherein the translating member further comprises at least one over-rotation protrusion and a rest-count protrusion protruding from the same face,
    the over-rotation protrusion further comprises a linear protrusion for engagement with one of the ribs after the first count wheel advances one increment, to inhibit the first count wheel from rotating further and the rest-count protrusion is configured to engage the ribs of the first count wheel when the translating member is in its initial position, thereby inhibiting movement of the first count wheel in the counting direction when the inhaler is in a rest state.

2. The inhaler of claim 1, wherein the pawl rotates the first count wheel by about 36° upon each actuation.

3. The inhaler of claim 1, wherein the first count wheel engages the intermediate wheel once for each full rotation through about 360° of the first count wheel.

4. The inhaler of claim 1, wherein the intermediate wheel rotates the second count wheel by between about 9° and 180° upon each actuation.

5. The inhaler of claim 1, wherein the first count wheel includes curved teeth with notches therebetween for receiving and engaging the pawl.

6. The inhaler of claim 1, wherein the first count wheel includes a set of first count numbers displayed annularly thereon, and the second count wheel includes a set of second count numbers displayed annularly thereon.

7. The inhaler of claim 6, wherein the first count numbers include numbers 0 to 9 and are arranged sequentially along a front face of the first count wheel, the first count wheel being incremented by $\frac{1}{10}^{th}$ of a full rotation upon each actuation by the pawl, and the second count numbers include numbers 0 to 12 and are arranged sequentially along a front face of the second count wheel, the second count wheel being incremented by $\frac{1}{12}^{th}$ of a full rotation upon each actuation by the intermediate wheel.

8. The inhaler of claim 1, wherein a front face of at least one of the first count wheel or the second count wheel includes a low dose indicator.

9. The inhaler of claim 1, wherein the counter includes a zero dose indicator.

10. The inhaler of claim 1, wherein the first count wheel includes a single notch on a periphery thereof, the second count wheel includes a plurality of notches arranged between annularly spaced teeth along an outer periphery of the second count wheel, and the intermediate wheel includes a first set of teeth for engaging both the notch of the first count wheel and one of the notches of the second count wheel, and a second set of teeth for only engaging one of the notches of the second count wheel, wherein the teeth of the second set of teeth are interspersed with the teeth of the first set of teeth on the intermediate wheel.

11. The inhaler of claim 1, wherein the dose counting mechanism further comprises a counter chassis configured to receive and to guide motion of the translating member.

12. The inhaler of claim 11, wherein the counter chassis comprises two channels, one along each of two opposed edges thereof, and the translating member further comprises at least a pair of tabs, at least one pair of tabs protruding from each of two opposed edges thereof, the tabs being received and movable in the channels of the counter chassis to enable linear movement of the translating member.

13. The inhaler of claim 1, wherein the over-rotation protrusion is configured to move linearly back to its initial position and is withdrawn from abutment with the rib of the first count wheel as the translating member returns to its initial position, thus freeing the count wheel to rotate again in the counting direction when actuated.

14. The inhaler of claim 1, further comprising a canister containing a medicament, the medicament including at least one active pharmaceutical ingredient and a propellant.

15. The inhaler of claim 14, wherein the medicament includes at least a first active pharmaceutical ingredient and a second active pharmaceutical ingredient, and the propellant includes at least one of HFA 227 (1,1,1,2,3,3,3-heptafluoropropane) or HFA 134a (1,1,1,2-tetrafluoroethane).

16. The inhaler of claim 14 further comprising a loading member having a spring for applying a compressive force to the canister.

17. The inhaler of claim 1, wherein the dispensing mechanism further comprises a releasable locking arrangement for locking the dispensing mechanism to prevent actuation thereof.

18. The inhaler of claim 17, further comprising a breath actuation mechanism and a manual actuation button, each for releasing the releasable locking arrangement thereby enabling actuation of the dispensing mechanism.

19. The inhaler of claim 1, further comprising:

a resetting member configured for movement between a first position and a second position to reset the dispensing mechanism after actuation, and a prevention mechanism having a pair of mutually engaging members, at least one of the engaging members configured to resiliently flex, under load, into abutment with a rigid component of the inhaler, wherein:

if movement of the resetting member is reversed when the resetting member has moved only partially from the first position to the second position, the mutually engaging members engage and the at least one of the engaging members flexes into abutment with the rigid component, to inhibit the dispensing mechanism from dispensing another dose of medicament until the resetting member is fully moved to the second position.

* * * * *